(12) United States Patent
Fink

(10) Patent No.: US 7,101,044 B2
(45) Date of Patent: Sep. 5, 2006

(54) AUTOMATED OBJECTIVE CHARACTERIZATION OF VISUAL FIELD DEFECTS IN 3D

(75) Inventor: Wolfgang Fink, Montrose, CA (US)

(73) Assignee: California Institute of Technology, Pasadena, CA (US)

( * ) Notice: Subject to any disclaimer, the term of this patent is extended or adjusted under 35 U.S.C. 154(b) by 367 days.

(21) Appl. No.: 10/430,367

(22) Filed: May 5, 2003

(65) Prior Publication Data

US 2004/0125341 A1 Jul. 1, 2004

Related U.S. Application Data

(63) Continuation-in-part of application No. 10/178,966, filed on Jun. 25, 2002, now Pat. No. 6,769,770, which is a continuation-in-part of application No. 09/820,283, filed on Mar. 27, 2001, now Pat. No. 6,578,966.

(60) Provisional application No. 60/379,155, filed on May 3, 2002, provisional application No. 60/251,957, filed on Dec. 7, 2000, provisional application No. 60/250,901, filed on Dec. 1, 2000, provisional application No. 60/204,362, filed on May 15, 2000, provisional application No. 60/192,645, filed on Mar. 27, 2000.

(51) Int. Cl.
*A61B 3/10* (2006.01)

(52) U.S. Cl. .................................................. 351/211

(58) Field of Classification Search ............... 351/211, 351/222, 223, 237, 239, 240, 242, 243, 246; 600/558

See application file for complete search history.

(56) References Cited

U.S. PATENT DOCUMENTS

| | | | |
|---|---|---|---|
| 5,176,147 A * | 1/1993 | Bodis-Wollner | ............ 600/558 |
| 5,589,897 A | 12/1996 | Sinclair et al. | |
| 6,260,970 B1 | 7/2001 | Horn | |
| 6,513,931 B1 | 2/2003 | Torrey et al. | |
| 6,572,229 B1 | 6/2003 | Wei | |

* cited by examiner

*Primary Examiner*—George Manuel
(74) *Attorney, Agent, or Firm*—Christie, Parker & Hale, LLP.

(57) ABSTRACT

A method and apparatus for electronically performing a visual field test for a patient. A visual field test pattern is displayed to the patient on an electronic display device and the patient's responses to the visual field test pattern are recorded. A visual field representation is generated from the patient's responses. The visual field representation is then used as an input into a variety of automated diagnostic processes. In one process, the visual field representation is used to generate a statistical description of the rapidity of change of a patient's visual field at the boundary of a visual field defect. In another process, the area of a visual field defect is calculated using the visual field representation. In another process, the visual field representation is used to generate a statistical description of the volume of a patient's visual field defect.

18 Claims, 21 Drawing Sheets

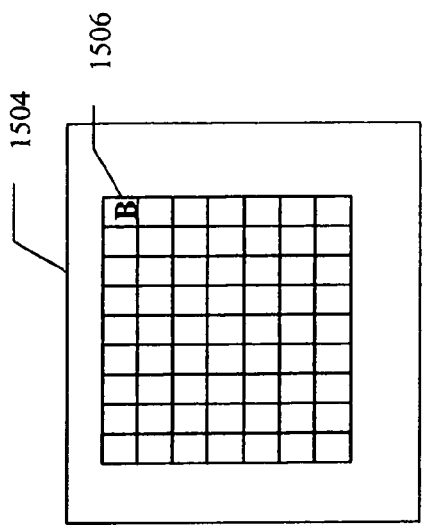
FIG. 15b
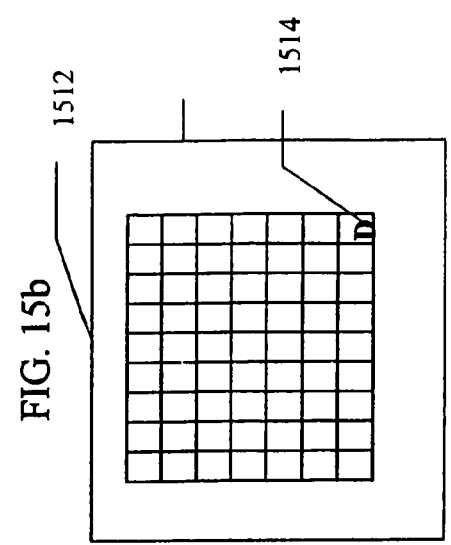
FIG. 15d
FIG. 15a
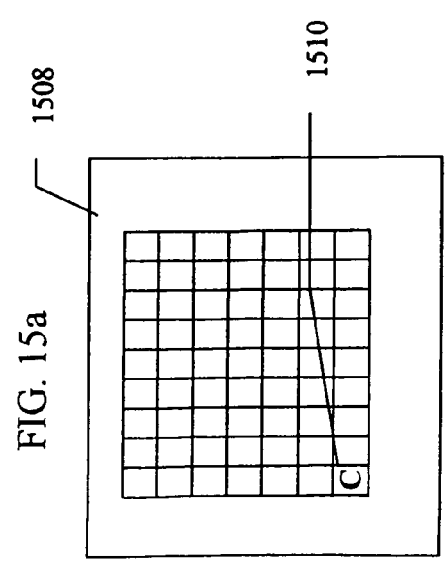
FIG. 15c

AUTOMATED OBJECTIVE CHARACTERIZATION OF VISUAL FIELD DEFECTS IN 3D

CROSS-REFERENCE TO RELATED APPLICATION

The present application claims the benefit of U.S. Provisional Patent Application No. 60/379,155, filed May 3, 2002, and is a continuation-in-part of co-pending U.S. patent application Ser. No. 10/178,966, filed Jun. 25, 2002, now issued as U.S. Pat. No. 6,769,770 on Aug. 3, 2004, which is a continuation-in-part of co-pending U.S. patent application Ser. No. 09/820,283, filed Mar. 27, 2001, now issued as U.S. Pat. No. 6,578.966 on Jun. 17, 2003, which claims the benefit of U.S. Provisional Application No. 60/192,645, filed Mar. 27, 2000, U.S. Provisional Application No. 60/204,362, filed May 15, 2000, U.S. Provisional Application No. 60/250,901, filed Dec. 1, 2000, and U.S. Provisional Application No. 60/251,957, filed Dec. 7, 2000, each of which are expressly incorporated by reference as though fully set forth in full herein.

STATEMENT REGARDING FEDERALLY SPONSORED RESEARCH OR DEVELOPMENT

The U.S. Government has certain rights in this invention pursuant to grant PHY-9722428 awarded by the National Science Foundation and 01 STCR R.03.021.048 awarded by NASA.

BACKGROUND OF THE INVENTION

This invention relates generally to the field of medical instrumentation and more specifically to the automated detection of defects of the retina, the optic nerve, and the brain's visual pathways.

A large number of medical ailments manifest themselves as defects in a patient's visual field. Patients suffering from, for example, macular degeneration, anterior ischemic optic neuropathy (AION), glaucoma, optic neuritis, detached retina, macular edema, central or branch retinal artery occlusion, some genetic impairments, and brain tumors may experience losses in visual acuity and visual field.

Non-invasive methods to measure a patient's visual field have been developed. For example, perimetry and campimetry provide information pertaining to the borderline between seeing and non-seeing areas within a patient's visual field.

Visual field tests employing visual field test patterns, such as an Amsler grid, have been developed to give a qualitative analysis of a patient's visual field. However such tests do not provide data of sufficient resolution or precision to perform a quantitative analysis of a patient's condition.

Recent developments of testing methods using visual field test patterns have included adjusting a patient's perception of the contrast levels within a visual field test pattern. For example, a method disclosed in U.S. Pat. No. 4,818,091, the disclosure of which is hereby incorporated by reference, requires the use of eyeglasses with polarized lenses to adjust the apparent contrast level of an Amsler grid.

These methods suffer from a variety of problems. Some methods require a patient to endure a long and boring testing process during which time the patient's concentration may lag because of fatigue. Other methods, while capable of being quickly performed, do not provide the spatial and contrast resolution required for high quality quantitative analysis.

Therefore, a need exists for a method that is quicker, simpler and more revealing than existing methods for characterizing the visual field. The present invention meets such need.

SUMMARY OF THE INVENTION

In various aspects of the invention, a method and apparatus for electronically performing a visual field test for a patient are provided. A visual field test pattern is displayed to the patient on an electronic display device and the patient's responses to the visual field test pattern are recorded. A visual field representation is generated from the patient's responses. The visual field representation is then used as an input into a variety of automated diagnostic processes. In one diagnostic process, the visual field representation is used to generate a statistical description of the rapidity of change of a patient's visual field at the boundary of a visual field defect. In another diagnostic process, the area of a visual field defect is calculated using the visual field representation. In another diagnostic process, the visual field representation is used to generate a statistical description of the volume of a patient's visual field defect.

In one aspect of the invention, a data processing apparatus for objectively characterizing a patient's visual field, includes a processor and a memory coupled to the processor and having program instructions executable by the processor stored in the memory. The program instructions include repeating the following steps a and b for a plurality of varying contrast levels and a plurality of corresponding patient response signals: a) presenting a visual field test pattern to the patient using an electronic display device, the visual field test pattern presented at a contrast level selected from the plurality of varying contrast levels; and b) receiving a corresponding patient response signal. The data processing system then generates a characterization of the patient's visual field using the plurality of contrast levels and the plurality of corresponding patient response signals.

In another aspect of the invention the characterization includes a statistical description of a boundary of a visual field defect.

In another aspect of the invention, the statistical description includes a percentage of retinal contrast sensitivity loss over degrees of visual field expressed as a slope of a line.

In another aspect of the invention, the statistical description further includes a mean of a plurality of slopes.

In another aspect of the invention, the statistical description further includes a distribution of a plurality of slopes.

In another aspect of the invention, the characterization includes an area of a visual field defect at a specified contrast sensitivity.

In another aspect of the invention, the characterization includes a volume of a visual field defect.

In another aspect of the invention, the program instructions further include generating a diagnosis by comparing the statistical characterization to a set of statistical characterizations associated with known causes of visual field defects.

In another aspect of the invention, the program instructions further included monitoring the progression of a visual field defect in the patient's visual field by comparing the statistical characterization to a set of statistical characterizations associated with the patient.

BRIEF DESCRIPTION OF THE DRAWINGS

These and other features, aspects, and advantages of the present invention will become better understood with regard to the following descriptions and accompanying drawings where:

FIGS. 15a, 15b, 15c, and 15d are depictions of visual field test patterns with peripheral fixation points in accordance with an exemplary embodiment of the present invention;

DETAILED DESCRIPTION

Figure 1:
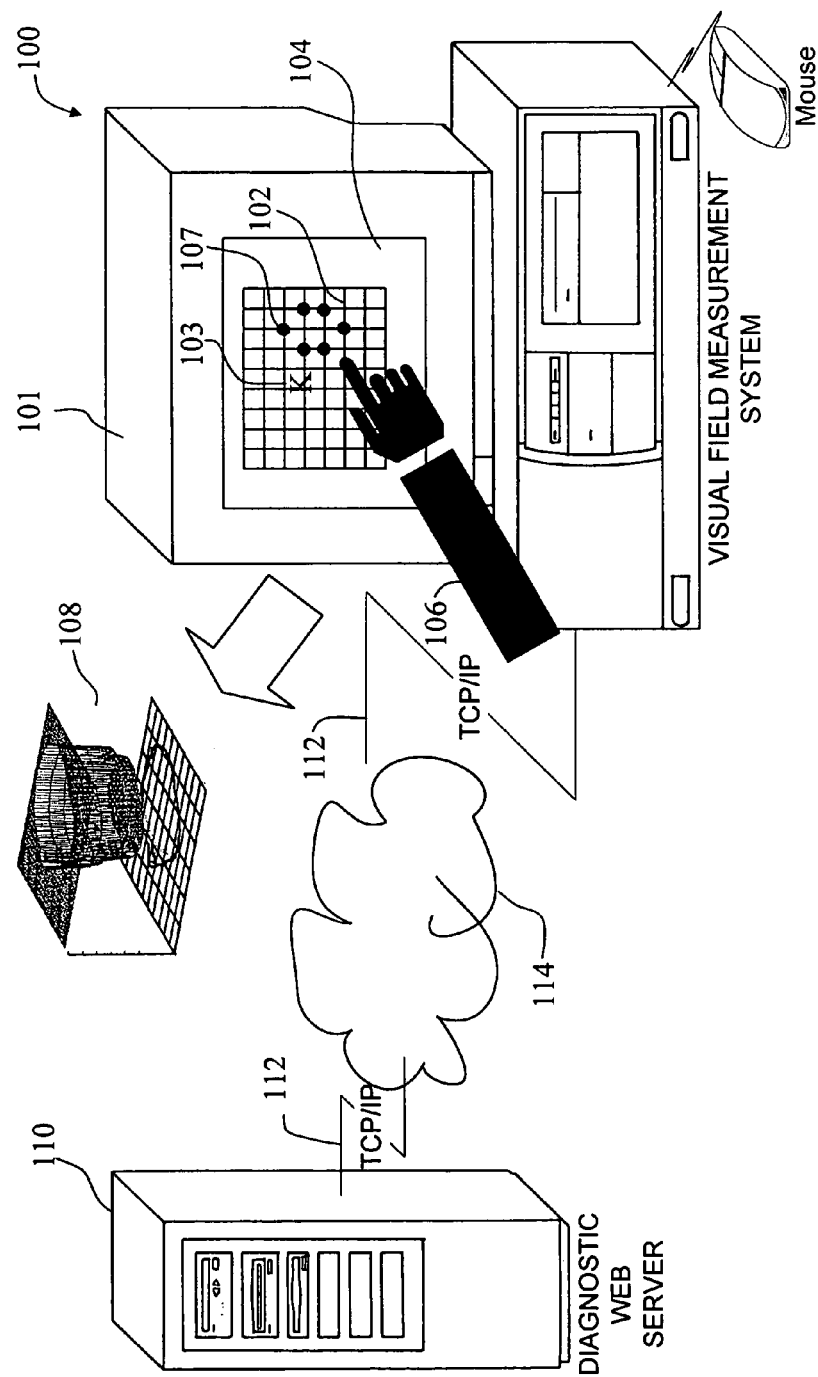
FIG. 1 is a depiction of an embodiment of a visual field measurement system according to the present invention.

FIG. 1 is a depiction of an embodiment of a visual field measurement system according to the present invention. A visual field measurement system 100 comprises a computer system with an electronic display 101 upon which a visual field test pattern 102 including a variable fixation point 103 is displayed. A patient response input device such as a touchscreen 104 is used to record for a patient's 106 response to the displayed visual field test pattern.

In operation, examination of a patient occurs in an examination room with a controlled ambient brightness. The patient is positioned in front of the electronic display at a fixed distance thus determining the angle of the patient's visual field. The patient's eye not under examination is covered with an eye-cover.

A visual field test pattern is displayed at a preselected contrast and angular resolution to the patient using the electronic display. The patient responds to the display of the visual field test pattern by selecting locations 107 within the field test pattern between areas where the patient clearly sees the visual field test pattern and areas where the patient is having difficulty seeing the visual field test pattern. The patient's responses are recorded and a visual field representation 108 is generated for diagnostic purposes.

In another embodiment of a visual field measurement system according to the present invention, analysis of the patient's responses or the visual field representation occurs at a remote analysis Web server site 110. The visual field measurement system is operably coupled to the Web server via communication links 112 adapted for communications using Transmission Control Protocol/Internet Protocol (TCP/IP) protocols such as Hyper Text Transfer Protocol (HTTP) via a communications network such as a Local Area Network (LAN) or a Wide Area Network (WAN) exemplified by Internet 114. The analysis Web server receives the patient's responses or the visual field representation and makes a comparison to previously received patients' responses or visual field representations. From the comparison, a diagnosis can be made of the patient's medical condition.

FIGS. 15a, 15b, 15c, and 15d are depictions of visual field test patterns with peripheral fixation points in accordance with an exemplary embodiment of the present invention. Visual field test patterns with peripheral fixation points allow testing for diseases that manifest themselves in the central vision of a patient, such as macular degeneration, and for testing of larger visual fields with higher eccentricities. Visual field test pattern 1500 includes peripheral variable fixation point 1502 in an upper right-hand corner of visual field test pattern 1500. Configured in this manner, visual field test pattern 1500 permits testing of a lower right quadrant of a patient's visual field. Visual field test pattern 1504 includes peripheral variable fixation point 1506 in an upper right-hand corner of visual field test pattern 1504. Configured in this manner, visual field test pattern 1504 permits testing of a lower left quadrant of a patient's visual field. Visual field test pattern 1508 includes peripheral variable fixation point 1510 in a lower left-hand corner of visual field test pattern 1508. Configured in this manner, visual field test pattern 1508 permits testing of an upper right quadrant of a patient's visual field. Visual field test pattern 1512 includes peripheral variable fixation point 1514 in a lower left-hand corner of visual field test pattern 1512. Configured in this manner, visual field test pattern 1512 permits testing of an upper left quadrant of a patient's visual field. In another embodiment of a visual field test pattern in accordance with an exemplary embodiment of the present invention, a plurality of peripheral fixation points are included in the visual field test pattern.

Figure 2:
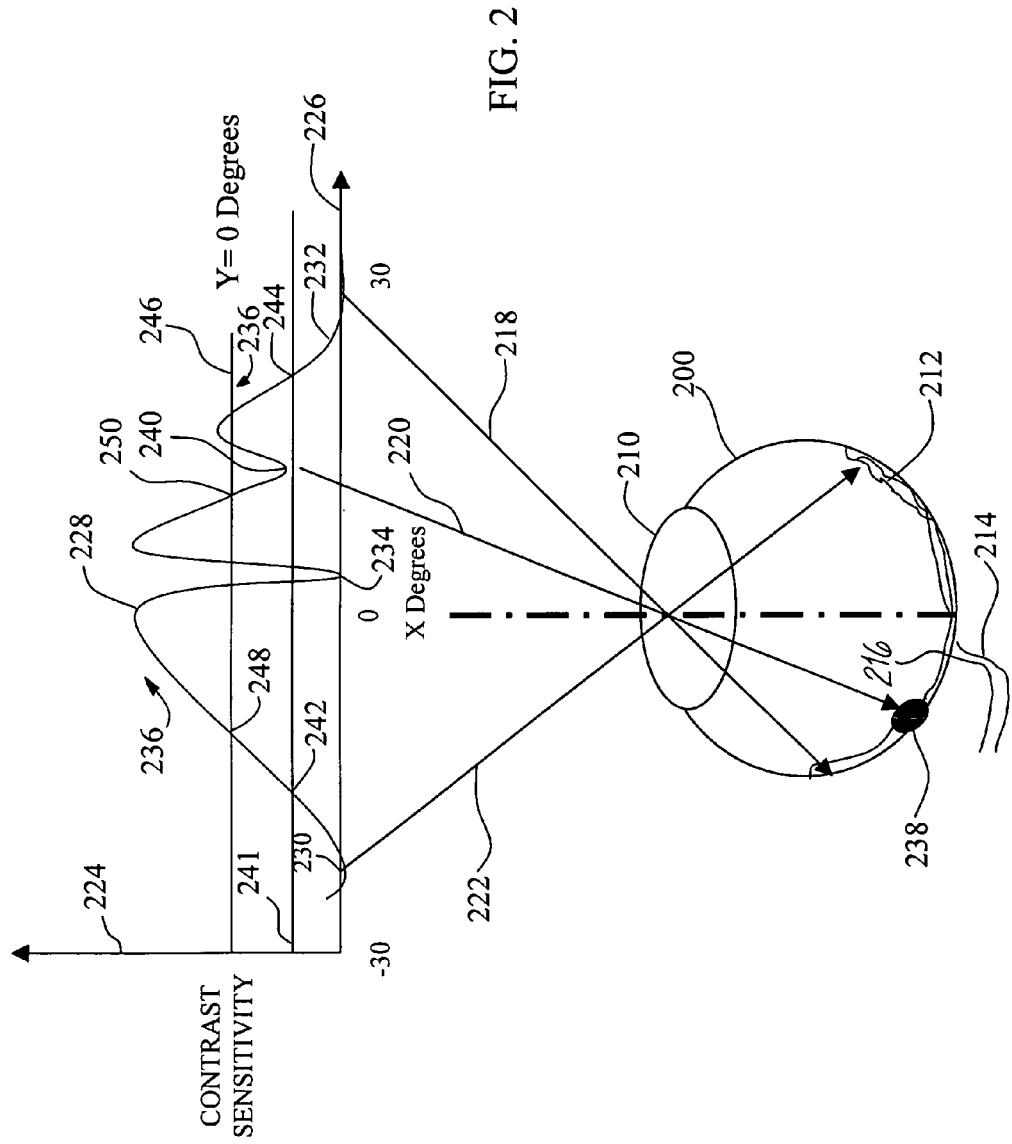
FIG. 2 is a depiction of a cross section of an eye showing retinal sensitivity within a retina's visual field.

FIG. 2 is a depiction of a cross section of an eye showing retinal sensitivity within a retina's visual field. An eye 200 partially comprises a cornea 210 and a retina 212. The cornea focuses light rays 218, 220, and 222 onto the retina. Cells within the retina transduce the incoming light rays into signals via a photochemical reaction. The resultant signals are transported from the retina to the brain for processing by an optic nerve 214. The optic nerve is coupled to the retina at the optic disk 216. The optic disk is not sensitive to light.

The contrast sensitivity of the retina varies from the perimeter of the retina to the center. The retina's contrast sensitivity is highest at the retina's center and lowest at the retina's perimeter. When plotted along a Y axis 224 versus the eccentricity of the retina's visual field in Degrees along an X axis 226, the contrast sensitivity of the retina describes a contrast sensitivity curve 228 with several local maxima and minima.

Two contrast sensitivity curve local minima are located on the portion of the contrast sensitivity curve corresponding to the retina's perimeter of the retina 230 and 232. One contrast sensitivity curve local minimum 234 is located at the portion of the contrast sensitivity curve associated with the retina's optical disk. As one moves from the perimeter of the retina to the center of the retina, the sensitivity of the retina increases 236.

Defects in the retina may cause the retina to lose its contrast sensitivity 240 either partially or totally. This loss in contrast sensitivity translates into defects in the visual field. Thus, defects in the retina can be detected by measuring the retina's visual field. Additionally, defects in the optic nerve or in a patient's ability to process visual information in the brain may also cause defects in the visual field.

The contrast sensitivity of the retina and pathways can be measured by presenting visual field test patterns of differing contrast to a patient. For example, if a first visual field test pattern has a high contrast level, as represented by a first constant contrast sensitivity 241, the retina detects the visual field test pattern at locations, 242 and 244, on the contrast sensitivity curve corresponding to locations on the retina close to the retina's perimeter.

If a second visual field test pattern has a low contrast level, as represented by a second constant contrast sensitivity line 246, the retina detects the second visual field test pattern at contrast sensitivity curve locations, 248 and 250, corresponding to locations on the retina close to the retina's center. In this case, the second test pattern's contrast is too low to be detected by the defective portion of the retina 238.

Figure 3:
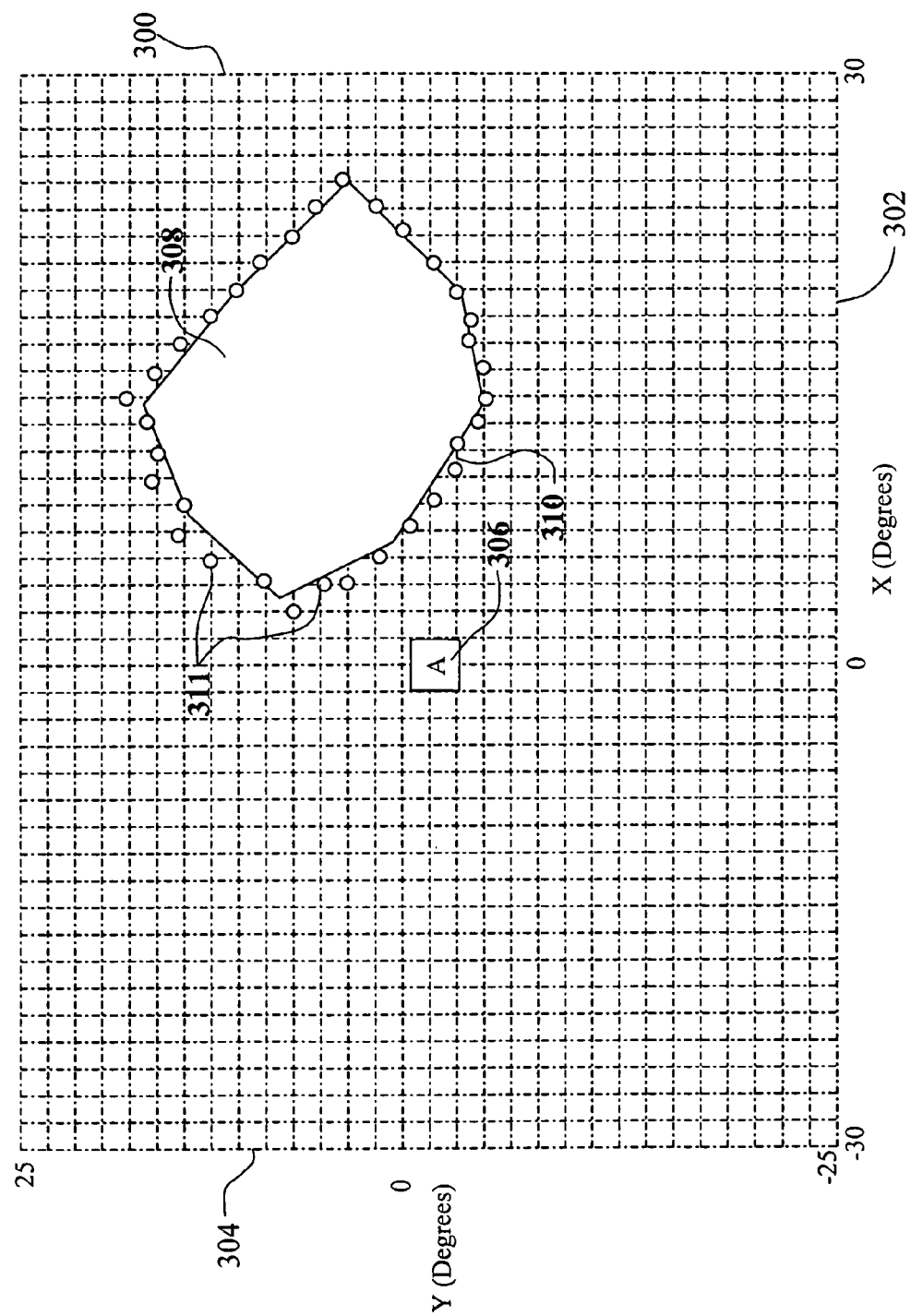
FIG. 3 is a depiction of an embodiment of a visual field test pattern at a low contrast level used to measure a visual field defect according to an embodiment of the present invention.

FIG. 3 is a depiction of an embodiment of a visual field test pattern at a low contrast level used to measure a visual field according to an embodiment of the present invention. A visual field measurement system 100 (FIG. 1) presents the visual field test pattern to a patient using an electronic display 101 (FIG. 1). The visual field test pattern includes a series of vertical lines and horizontal lines substantially orthogonal to one another thus creating a rectilinear grid 300. The lines of the grid are distributed along an X axis 302 and a Y axis 304 such that when a patient views the visual field test pattern presented on the electronic display, the lines create a grid within the patient's visual field. The exact grid spacing is variable and dependent on testing conditions and clinician preference.

The appearance of a visual field defect is dependent on the type of defect present in the retina, optic nerve, or patient's visual processing abilities. In this case, a defect in the visual field is presented as an area 308 where the grid is not visible to the patient. The patient touches the electronic display at a perimeter location 310 corresponding to an edge of the area of the visual field defect. A location where the patient touches the electronic display is sensed by a touch screen 104 (FIG. 1) and recorded. The patient continues touching the perimeter of the area of the visual field defect describing a series of rectilinear locations recorded as the patient's response to the visual field test pattern. These rectilinear locations define a perimeter for the visual field defect at a single contrast level.

Figure 4:
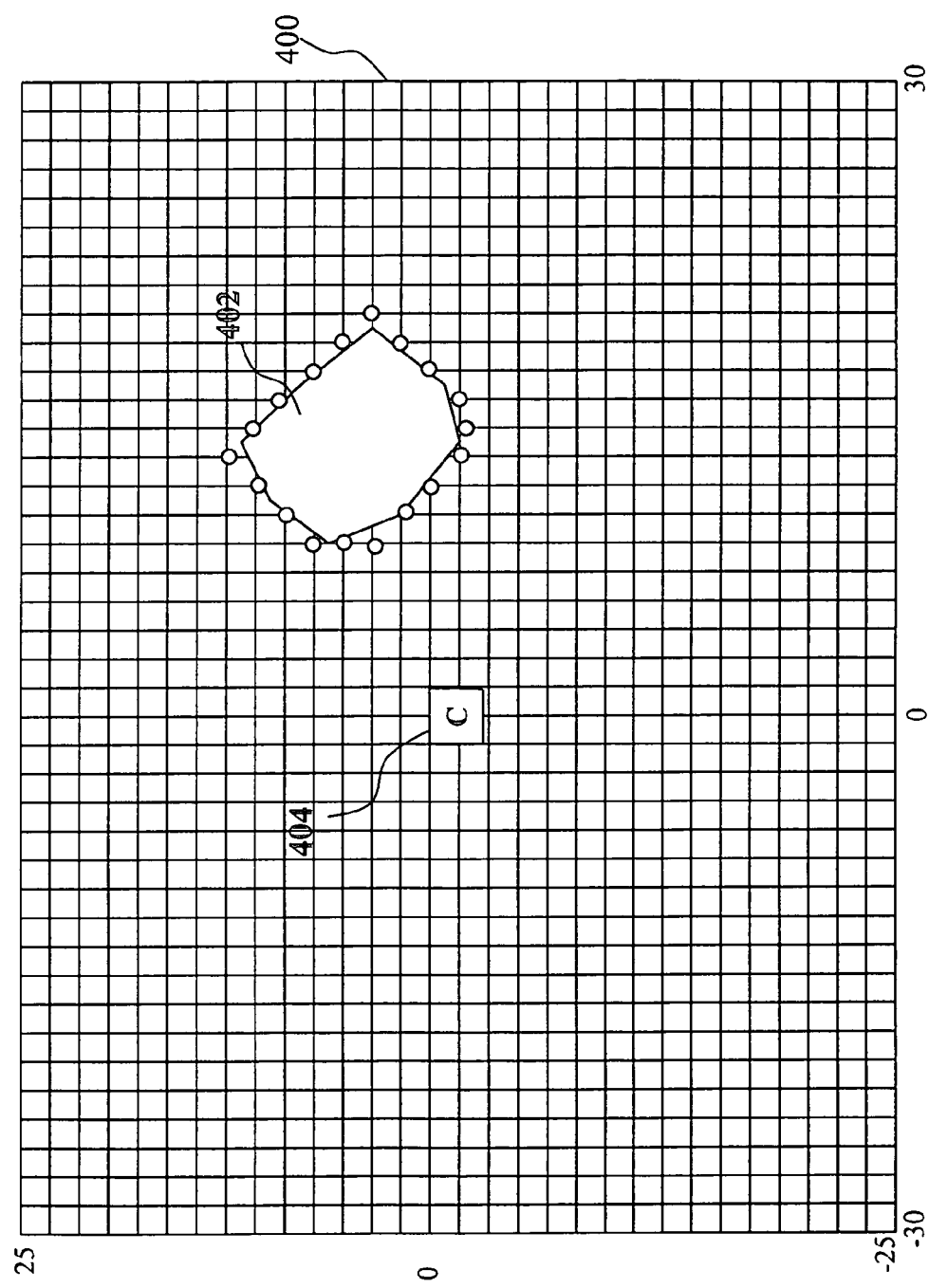
FIG. 4 is a depiction of an embodiment of a visual field test pattern at a high contrast level used to measure a visual field defect according to an embodiment of the present invention.

FIG. 4 is a depiction of an embodiment of a visual field test pattern at a high contrast level used to measure a visual field defect according to an embodiment of the present invention. The high contrast visual field test pattern has the same overall configuration of the previously described low contrast visual field test pattern but the high contrast visual field test pattern is presented to the patient at a high contrast level.

The visual field measurement system presents the visual field test pattern to the patient and the patient's response to the visual field test pattern is recorded as previously described. This time however, the patient may perceive that the defect in the visual field has grown smaller because the visual field test pattern has a higher contrast level and is thus easier to see.

In another embodiment of a visual field test pattern according to the present invention, the visual field test pattern is a rectilinear grid known as an Amsler grid.

In another embodiment of a visual field test pattern according to the present invention, a fixation point is presented to the patient and the fixation point is varied during the time the visual field test pattern is presented to the patient. For example, the fixation point may be a displayed letter and the displayed letter is randomly and constantly changed during the time the visual field test pattern is being presented to the patient.

In another embodiment of a visual field test pattern according to the present invention, the visual field test pattern is varied slightly during the testing period in order to mitigate a Troxler effect. Varying the visual field test pattern is accomplished be either changing the display position of the visual test pattern on a display device or by causing the visual field test pattern to flicker at a frequency selected to mitigate the Troxler effect.

In another visual field test pattern in accordance with an exemplary embodiment of the present invention, the color of the elements included in the visual field test pattern, such as the previously described grid lines and fixation points, is varied. For example, the visual test pattern can be presented in a single color, such as red, and the contrast levels are varied for the visual test pattern in order to elicit a patient response. In another example, the color of a visual field test pattern is varied, such as first presenting a visual field test pattern in red and then presenting the visual field test pattern in green, in order to elicit a patient response. In another example, both the contrast levels and the color are varied in order to elicit a patient response.

Figure 5:
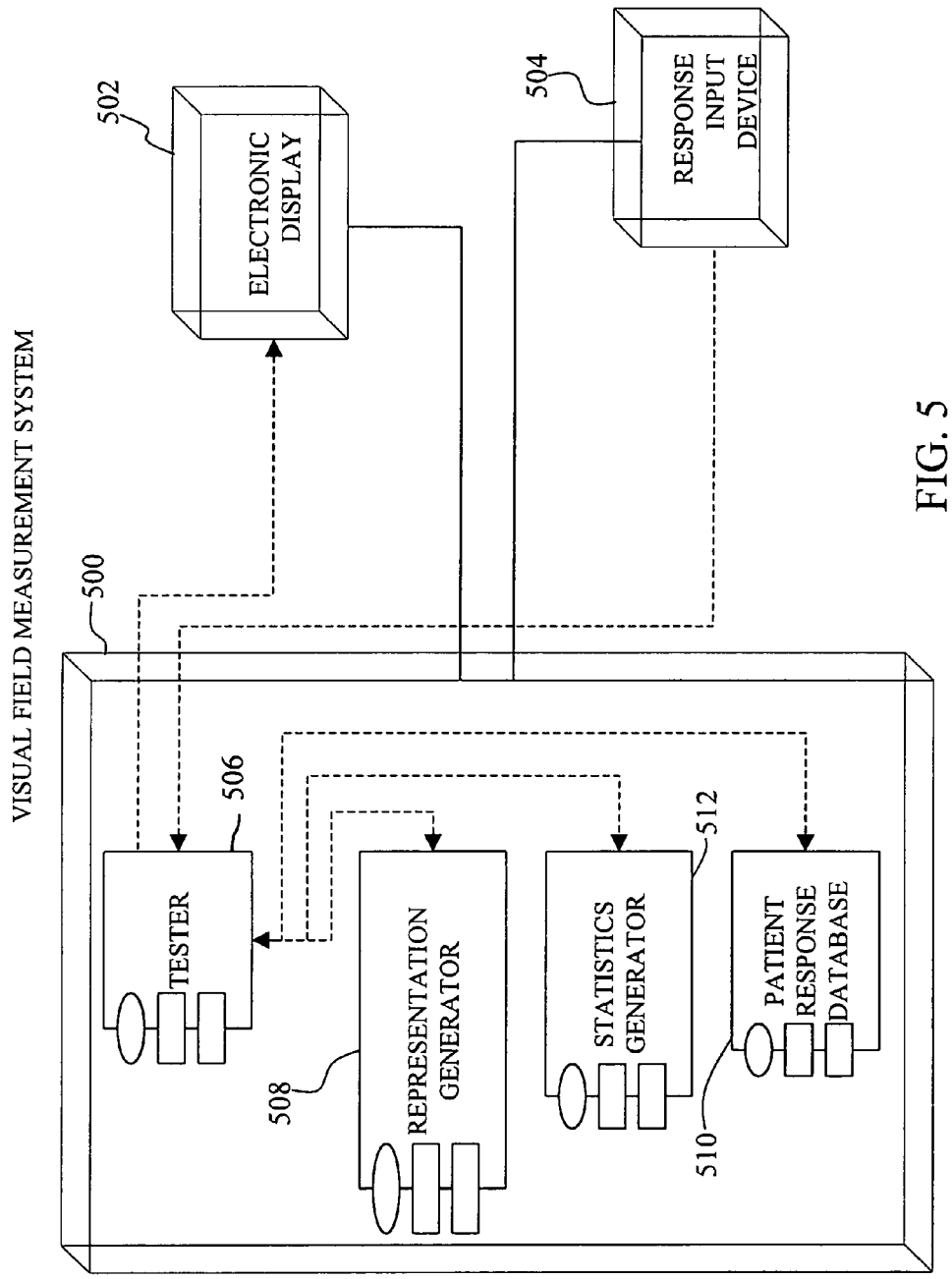
FIG. 5 is a deployment diagram of an embodiment of a visual field measurement system according to the present invention.

FIG. 5 is a deployment diagram of an embodiment of a visual field measurement system according to the present invention. A visual field measurement system comprises a central processor 500 operably coupled to an electronic display 502 and a patient response input device 504.

In one embodiment of a visual field measurement system, a personal computer is used with a conventional CRT display. The CRT display is modified with a touchscreen device so that a patient may simply touch the CRT display at the locations where the patient detects a change in the appearance of the visual field test pattern.

In another embodiment of a visual field measurement system, the touchscreen device is replaced by a pointing device, such as a trackball or mouse, operably coupled to a programmatically controlled cursor presented on the electronic display along with the visual field test pattern. The patient manipulates the cursor to outline the visual field defect.

In another embodiment of a visual field measurement system, the cursor is controlled through keyboard inputs.

In another embodiment of a visual field measurement system, a plurality of electronic displays and patient response input devices are operably coupled to a single central processor. In this case, a plurality of patients may be tested at a single time.

In other embodiments of visual field measurement systems, other electronic displays capable of displaying visual field test patterns at varying contrast levels are used such as projection screens, Liquid Crystal Displays (LCDs), plasma displays, etc.

The visual field measurement system further comprises software objects hosted by the central processor. The software objects include a tester 506 operably coupled to the electronic display and the patient response device. The tester generates visual field test patterns for display to the patient using the electronic display. The tester package receives patient response signals from the patient response input device and records patient responses generated from the patient response signals for use by a representation generator 508.

The representation generator accepts patient responses from the tester and generates a visual field representation from the patient response signals suitable for use in a diagnostic process.

In one embodiment of a visual field measurement system, the tester is operably coupled to a patient response database 510. The tester puts the patient response in the patient response database along with a patient identification and time and date information. A time series of stored patient responses taken over time from the same patient is then used to watch the progress of a patient's medical condition.

In another embodiment of a visual field measurement system, the tester puts visual field representations in the user response database. The stored visual field representations are used in the same manner as the patient responses as previously described.

In another embodiment of a visual field measurement system according to the present invention, the tester is operably coupled to a statistics generator 512. The statistics generator accepts patient responses or visual field representations and generates descriptive statistics useful for diagnostic purposes.

Figure 6:
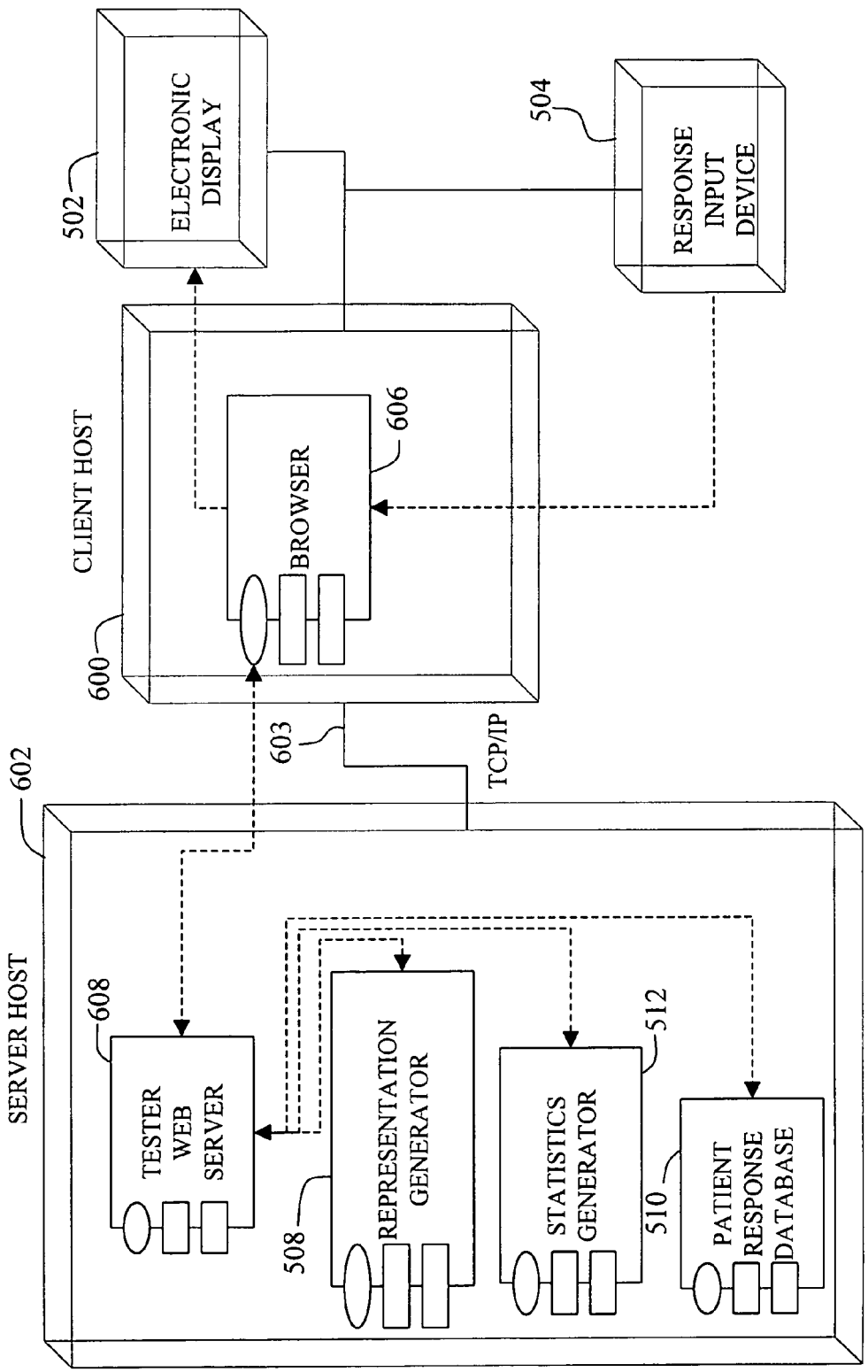
FIG. 6 is a deployment diagram of a Web based embodiment of a visual field measurement system according to the present invention.

FIG. 6 is a deployment diagram of a Web based embodiment of a visual field measurement system according to the present invention. A client host 600 is operably coupled to a server host 602 via a communications link 603 adapted for communications using TCP/IP. The client host is operably coupled to a previously described electronic display 502 and a previously described patient response input device 504. A browser 606 hosted by the client host is operably coupled to the electronic display and the patient response input device. The browser requests and receives Web pages from a tester Web server 608 hosted by the server host. The Web pages served from the tester Web server implement the previously described visual field measurement procedure.

The browser collects patient responses from the response input device and posts the results to the tester Web server. The tester Web server is operably coupled to a previously described representation generator 508, patient response database 510, and statistics generator 512. The tester Web server uses the representation generator to generate visual field representations from patient responses as previously described and incorporates the visual field representations into a Web page that is transmitted back to the browser for display.

Figure 7:
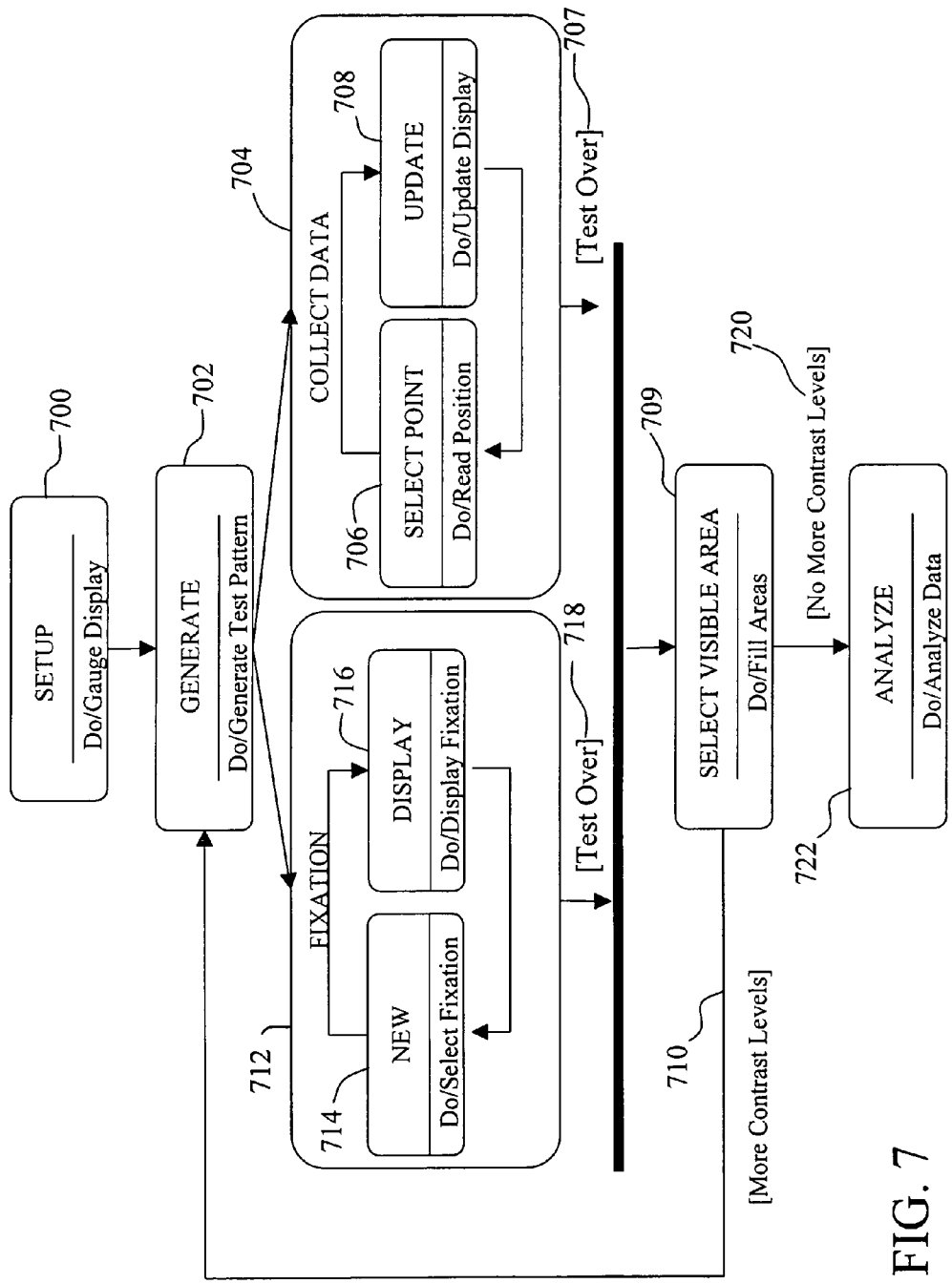
FIG. 7 is a state diagram for a tester object embodiment of a visual field measurement system according to the present invention.

FIG. 7 is a state diagram for a tester object embodiment of a visual field measurement system according to the present invention. A tester software object 506 (FIG. 5) performs a setup 700 of the electronic display including adjusting the size of the visual field test pattern based on the size of the electronic display and a distance between a patient and the electronic display. Patient information is collected for association with the patient response in the previously described patient response database.

A first contrast level is set and a visual field test pattern is generated 702 for the first contrast level. The visual field test pattern is presented to the patient and the collection of patient response signals from a previously described patient input device begins.

The tester collects data from the patient response input device by reading points 706 selected by the patient outlining the perimeter of any visual field defect observed by the patient. The tester updates 708 the electronic display by highlighting the points selected by the patient.

At the end of the test, a clinician or the patient selects an area of the visual field test pattern that the patient can see clearly 709. This indicates to the tester whether the areas of the visual field test pattern within the enclosed perimeter outlined by the patient are areas where the patient can see or not see the visual field test pattern. For example, in the previously described high contrast visual field test pattern 400 (FIG. 4), a patient cannot see the visual field test pattern within the area of the visual field defect 402 (FIG. 4). In this case, the clinician or patient selects an area of the visual field test pattern outside of the visual defect area to indicate that the patient can see that portion of the visual field test pattern.

The tester determines if there are more contrast levels to test 710 and returns to the visual field test pattern generation and contrast setting state 702 and the collect data state 704 until no more contrast levels are needed.

In another embodiment of a visual field measurement system according to the present invention, the screen update at update state 708 includes updating a cursor location indicating the position of a displayed cursor responsive to a user input device such as a pointing device or track ball.

In another embodiment of a visual field measurement system according to the present invention, a plurality of visual field test patterns with varying contrast levels are presented to a patient in order of decreasing or increasing contrast levels.

In another embodiment of a visual field measurement system according to the present invention, a plurality of visual field test patterns with varying contrast levels are presented to a patient in random order with respect to the varying contrast levels.

In another embodiment of a visual field measurement system according to the present invention, the visual field test pattern contains a variable fixation point as previously described. In this case, the tester simultaneously generates new fixation points 712 while the tester is collecting patient responses. The tester constantly determines a new 714 fixation point and displays 716 the new fixation point until the test is over 718.

If no more visual field test patterns for new contrast levels are to be generated 720, the tester moves into an analyze state 722 where the collected data is analyzed for diagnostic purposes.

Figure 8:
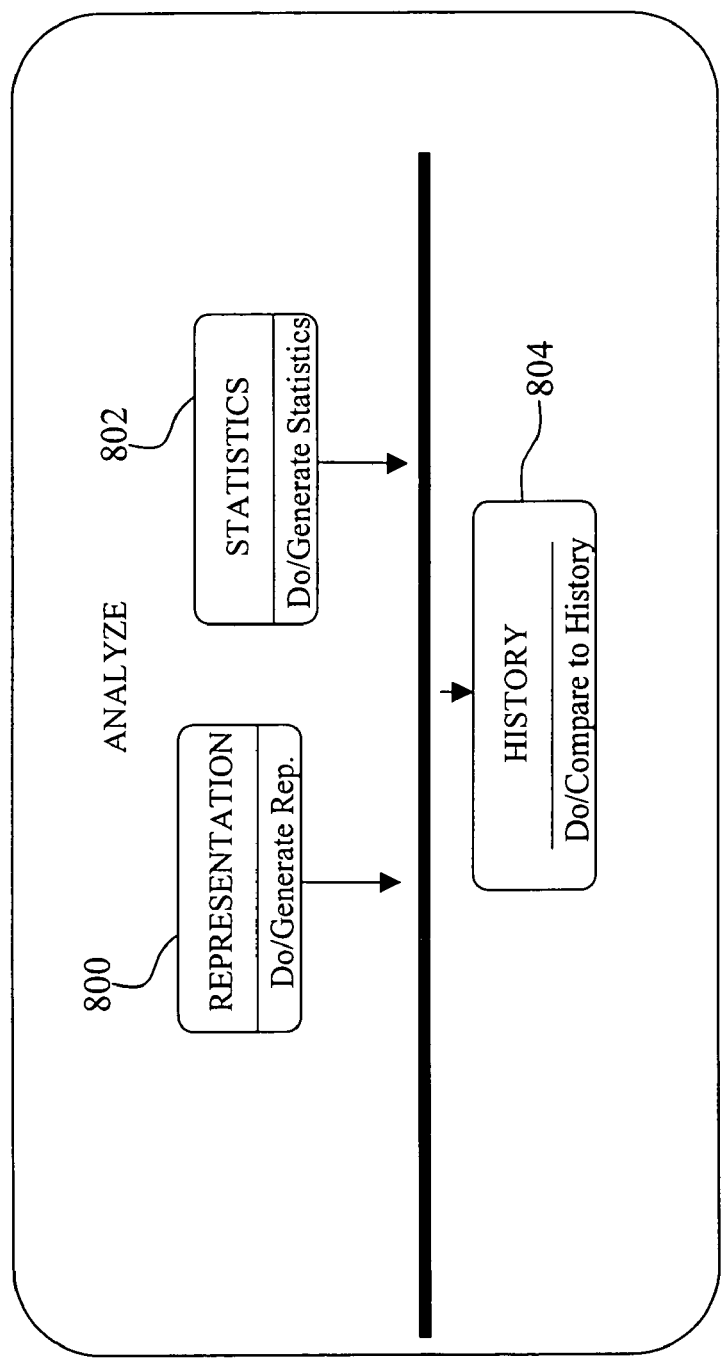
FIG. 8 is a state diagram for an analysis state embodiment of visual field measurement system according to the present invention.

FIG. 8 is a state diagram for an analysis state embodiment of visual field measurement system according to the present invention. In the analyze state, the tester generates a to be described visual field representation using the previously described patient response data 800. The visual field representation can be saved for use in further diagnostic processes or can be displayed directly to a clinician for diagnostic purposes.

Figure 9:
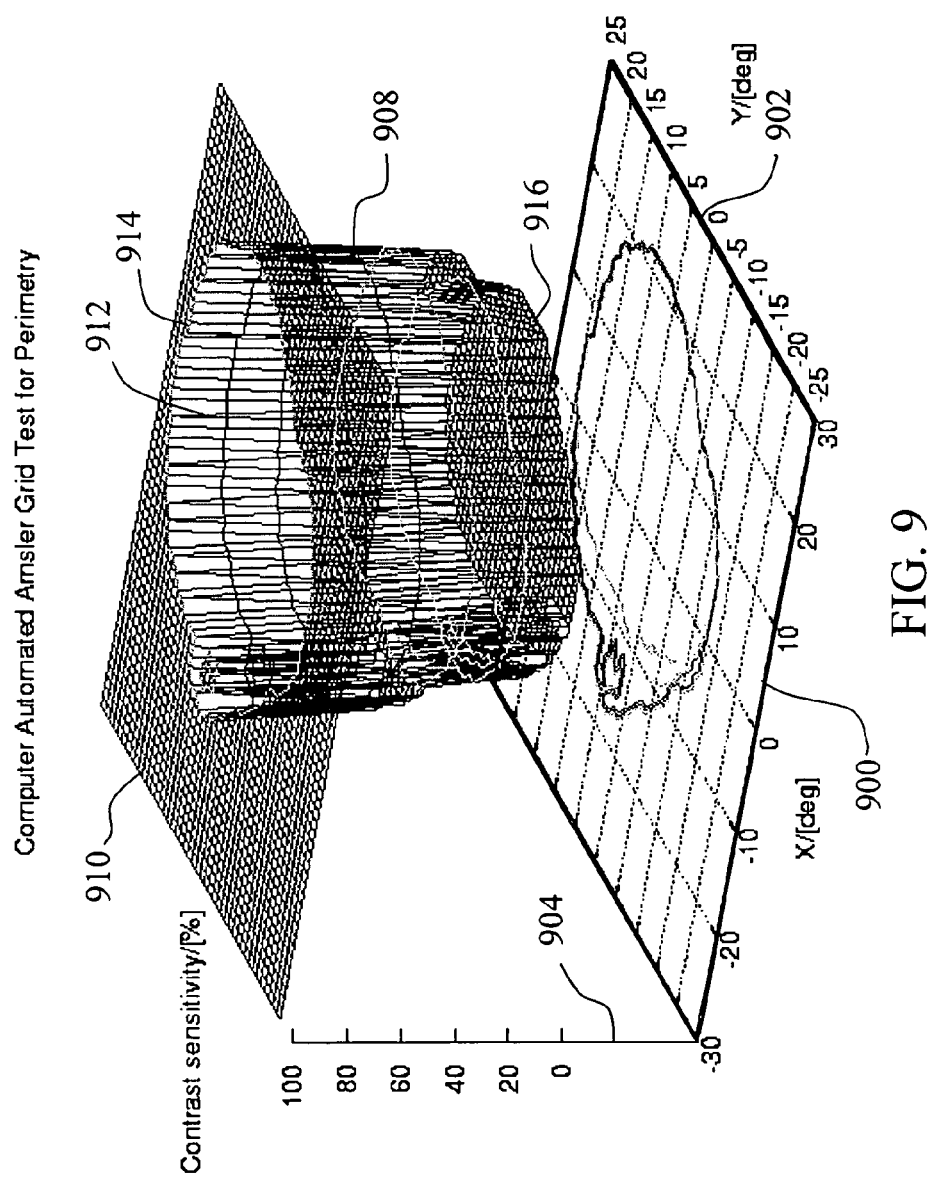
FIG. 9 is an exemplary visual field representation for a patient with "dry" macular degeneration generated from a patient response by an embodiment of a visual field measurement system according to the present invention.

FIG. 9 is an exemplary visual field representation generated by an embodiment of a visual field measurement system according to the present invention from a patient response. The visual field representation is a three-dimensional plot of contrast sensitivity 904 plotted across a two-dimensional visual field comprising an X axis 900 and a Y axis 902 demarcated in degrees. As previously described, a patient outlines visual field defects on a visual field test pattern displayed at a plurality of contrast levels. Each of these outlined visual field defects is plotted on a two-dimensional plane defined by the contrast sensitivity at which the visual field defect was outlined by the patient. This process creates a three-dimensional visual field representation 908 with great descriptive power. Returning to FIG. 8, the tester generates 802 a statistical description of the patient response. A statistical description of the patient response is used by a diagnostic tool to determine the severity of a visual field defect. A statistical description of a visual field defect is also useful for comparison of a visual field defect to historical data 804 collected from the patient.

Figure 10:
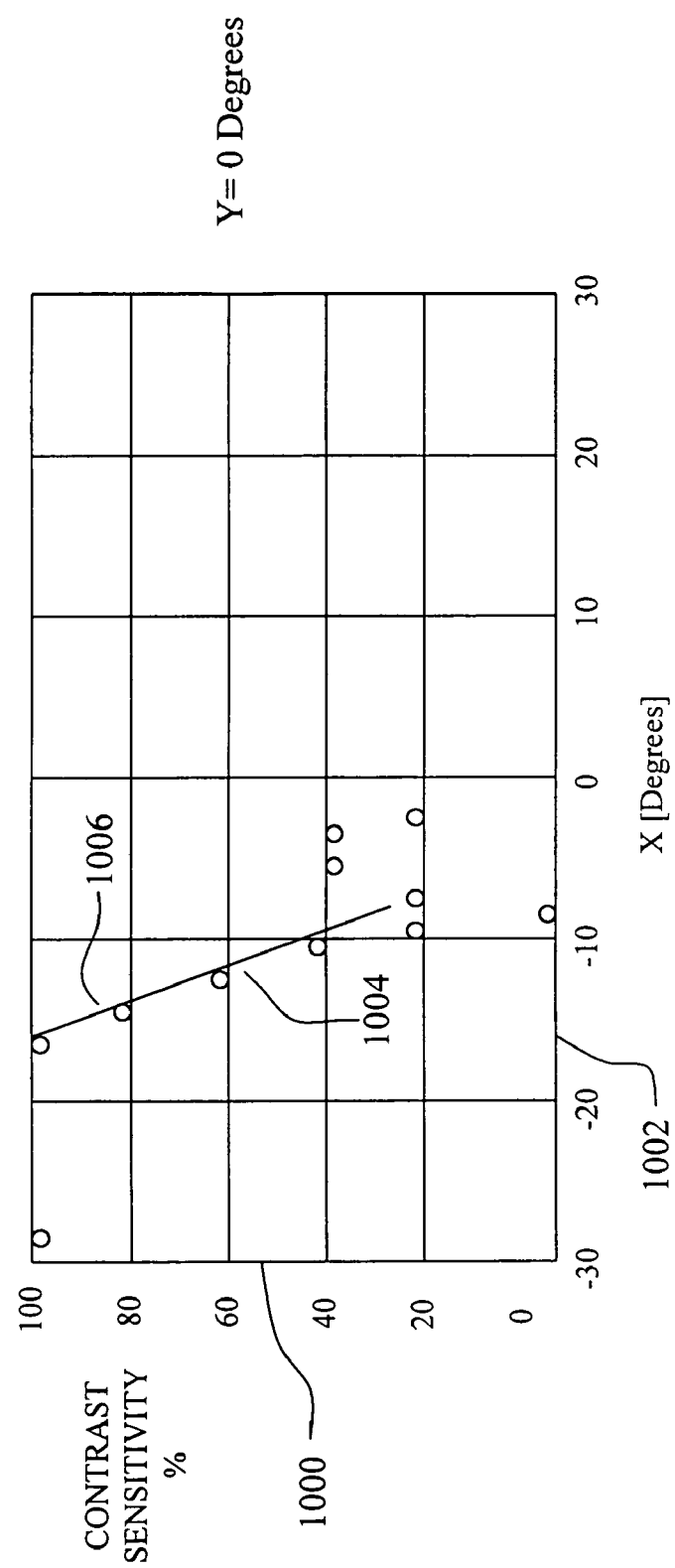
FIG. 10 is an exemplary output from an embodiment of a visual field measurement system according to the present invention illustrating the generation of a statistical description of a patient's response.

FIG. 10 is an exemplary output from an embodiment of a visual field measurement system according to the present invention illustrating the generation of a statistical description of a patient's response. In this example, the patient's response is transformed into a plot of retinal contrast sensitivity 1002 versus displacement along an X axis of the visual field. In this case, a defect in the visual field is shown by a decrease in contrast sensitivity 1004. A line 1006 generated through a linear regression process depicts the steepness of the decline in contrast sensitivity of the retina corresponding to the location of the visual field defect.

In another embodiment of a visual field measurement system according to the present invention, the visual field data is presented as a ratio between the loss of contrast sensitivity over degrees of visual field taken perpendicularly to the steepest or shallowest slope, expressed as a grade (% contrast sensitivity/degree).

As an example measure for the slope calculation a slope grade can be defined as the percentage of retinal contrast sensitivity loss over degrees of visual field. A shallow slope would then be characterized as a percentage of retinal contrast sensitivity loss along a larger number of degrees of visual field, whereas a steep slope would be characterized as a large percentage of retinal contrast sensitivity loss along only a few degrees of visual field. Applying the slope grade measure, all occurring slopes, e.g., parallel to an X-axis of the visual field, can then be automatically calculated. Having calculated all the occurring slopes in one direction the average slope and standard variation for that direction can be obtained. Furthermore, a histogram can be generated using all individual slopes for that direction, ranging from shallow to steep slopes, to actually result in a slope distribution. The same procedure outlined above can then be applied to other directions (e.g., parallel to a Y-axis of the visual field, or radially from the center of fixation).

Figure 16:
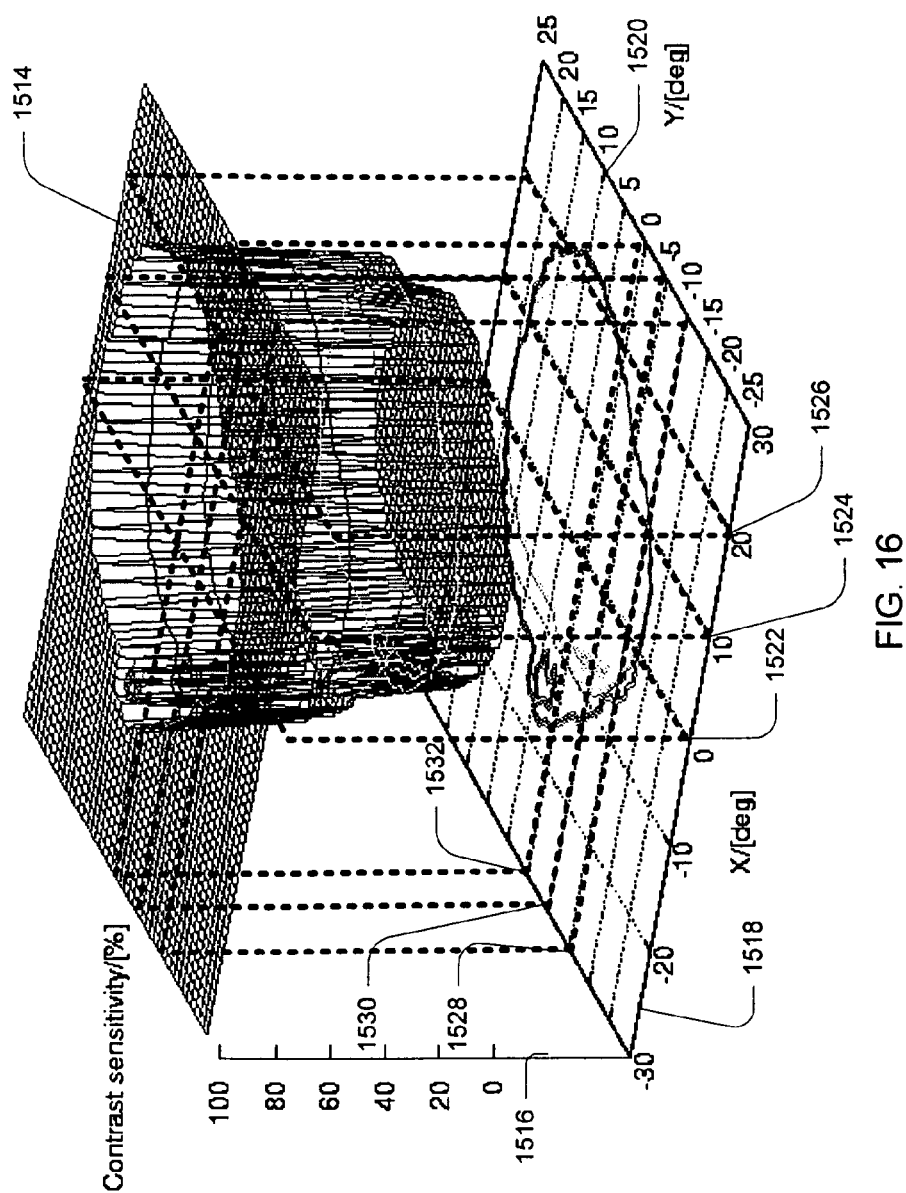
FIG. 16 is a diagram depicting determining slopes for a plurality of cross-sections parallel to a visual field axis through a visual field representation in accordance with an exemplary embodiment of the present invention.

FIG. 16 is a diagram depicting determining slopes for a plurality of cross-sections parallel to a visual field axis through a visual field representation in accordance with an exemplary embodiment of the present invention. Measurement of the change in contrast sensitivity with respect to displacement along an axis of a visual field may be determined in a plurality of locations. A visual field representation 1514 is displayed in a 3 dimensional graph with contrast sensitivity plotted along a vertical axis 1516, degrees of visual field in the X direction plotted along an X axis 1518, and degrees of visual field along a Y axis 1520. Cross sections may be taken through the visual field representation in a variety of ways and slopes determined along the cross-section as depicted in FIG. 10. For example, cross sections may be taken parallel to the Y axis such as cross sections 1522, 1524, and 1526. Cross-sections may also be taken parallel to the X axis such as cross-sections 1528, 1530, and 1532.

Figure 17:
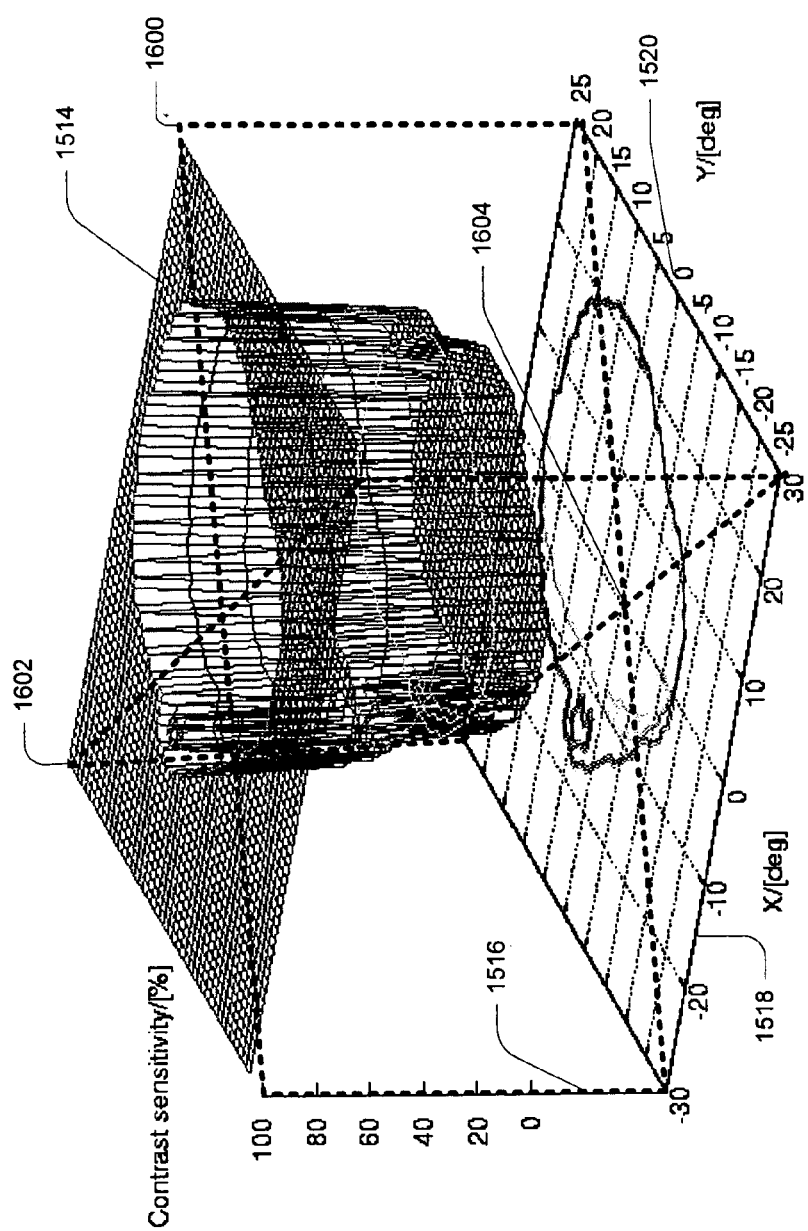
FIG. 17 is a diagram depicting determining slopes for a plurality of cross-sections through the center of a visual field representation in accordance with an exemplary embodiment of the present invention.

FIG. 17 is a diagram depicting determining slopes for a plurality of cross-sections through the center of a visual field representation in accordance with an exemplary embodiment of the present invention. Measurements of the change in contrast sensitivity with respect to displacement along the visual field may also be made using cross-sections through the center of a visual field representation. A visual field representation 1514 is displayed in a 3 dimensional graph with contrast sensitivity plotted along a vertical axis 1516, degrees of visual field in the X direction plotted along an X axis 1518, and degrees of visual field along a Y axis 1520. Cross sections may be taken through the visual field representation in a variety of ways and slopes determined along the cross-section as depicted in FIG. 10. For example, cross sections may be taken radially from the center of fixation 1604, such as cross-sections 1600 and 1602.

Figure 18:
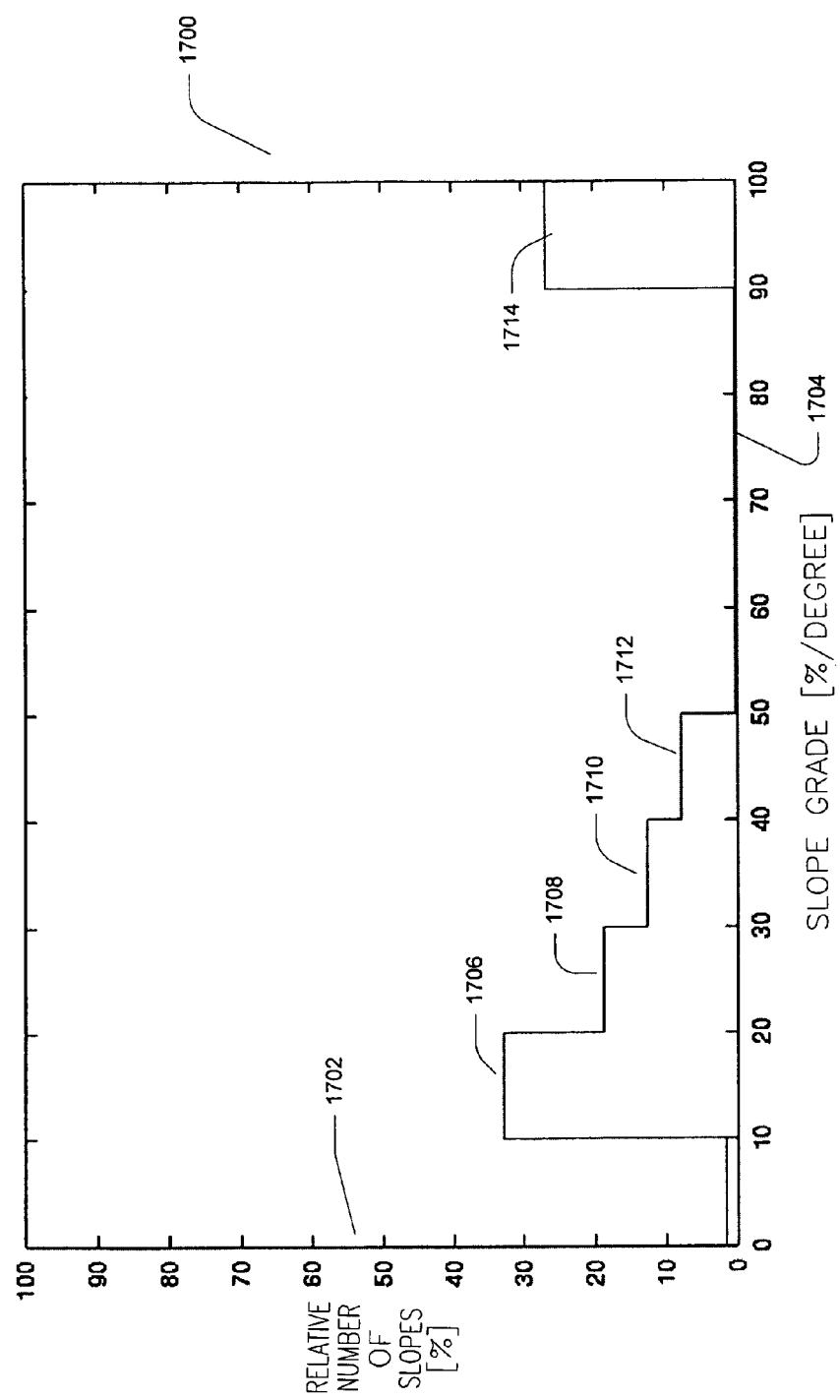
FIG. 18 is a histogram of a distribution of slopes determined from a visual field representation in accordance with an exemplary embodiment of the present invention.

FIG. 18 is a histogram of a distribution of slopes determined from a visual field representation in accordance with an exemplary embodiment of the present invention. A histogram 1700 may be generated for the slopes determined from a visual field representation. The histogram may be generated by plotting the relative number of slopes as a percentage along a Y-axis 1702 and slope grade defined as % contrast sensitivity per degree of visual field along an X axis 1704. This results in generating a histogram with a distinctive pattern that may be used as a statistical measure to compare one visual field representation to another. The comparison may be made between histograms generated from a single patient over time in order to monitor the progression of a visual field defect. The comparison may also be made between different patients, such as a first patient with a visual field defect having a known cause and a second patient having a visual field defect with an unknown cause in order to generate a diagnosis for the second patient.

Referring again to FIG. 9, in another embodiment of a visual field measurement system according to the present invention, a visual field defect is characterized by a ratio of an area of the visual field defect at a highest measured contrast sensitivity 914 versus an area of the visual field defect at a lowest measured contrast sensitivity 916.

Figure 19:
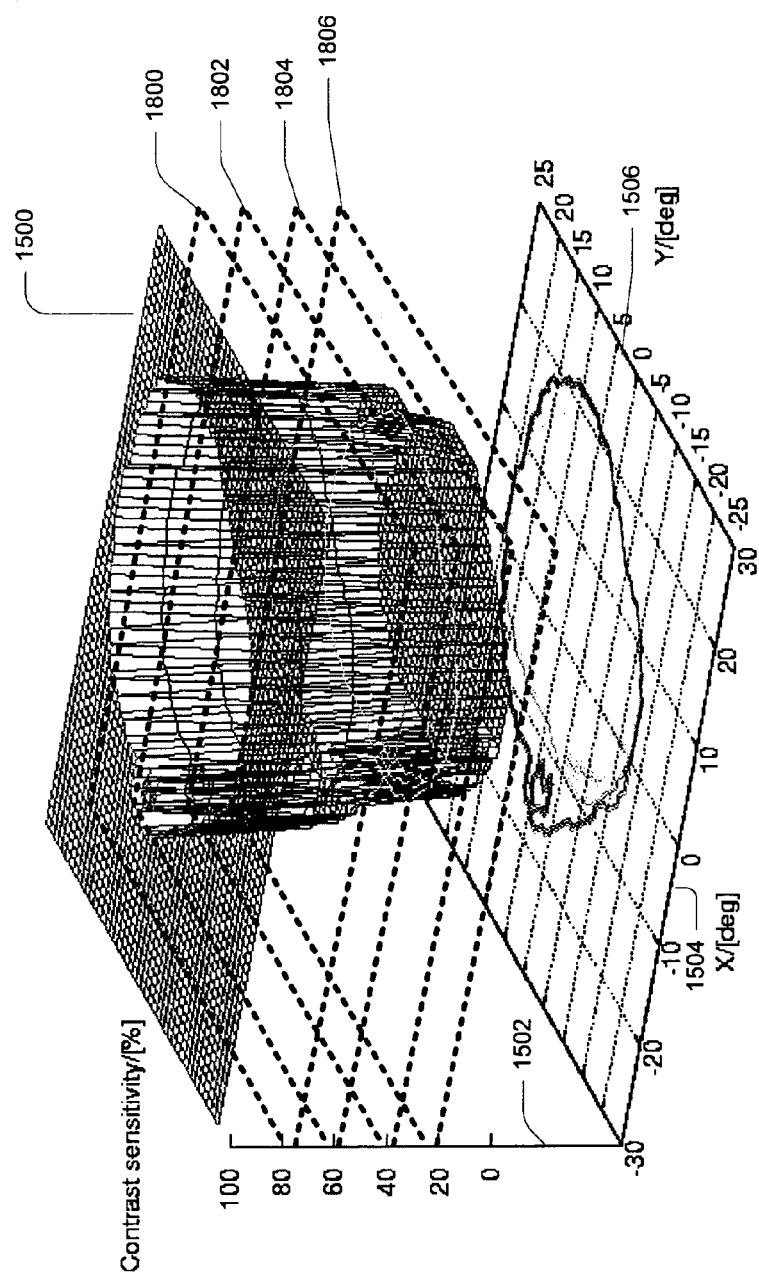
FIG. 19 is a diagram depicting determining a plurality of areas of visual field defects at a plurality of contrast sensitivity levels of a visual field representation in accordance with an exemplary embodiment of the present invention.

FIG. 19 is a diagram depicting determining a plurality of areas of visual field defects at a plurality of contrast sensitivity levels of a visual field representation in accordance with an exemplary embodiment of the present invention. A visual field representation 1514 is displayed in a 3 dimensional graph with contrast sensitivity plotted along a vertical axis 1516, degrees of visual field in the X direction plotted along an X axis 1518, and degrees of visual field along a Y axis 1520. Sections may be taken through the visual field representation at various percent contrast sensitivities, such as sections 1800, 1802, 1804, and 1806. The area of visual field loss as a function of contrast sensitivity can be calculated for these sections by automatically counting grid-points (usually one grid-point corresponds to an area of one $deg^2$) that have been marked by a patient and thus calculate the area of visual field loss at the presented contrast level. The percentage of visual field loss at a presented contrast level is calculated by dividing the number of marked grid-points by the total number of presented grid-points at that contrast level. In addition, an overall volume of visual field loss as compared to a "normal" hill-of-vision may be calculated by automatically counting all the grid-points of all presented contrast levels that have been marked by the patient and divide by the total number of grid-points of all presented contrast levels to obtain the percentage of volume of visual field loss compared to a "normal" hill-of-vision.

Referring again to FIG. 8, statistical descriptions of a patient's responses and visual field representations are used by the tester to track the progress of an ailment affecting the visual field. In a history 804 state, the tester generates time series of either statistical descriptions or visual field representations for use by a clinician in monitoring the progress of an ailment.

Visual field representations are used to create a diagnostic tool using artificial intelligence to diagnose a patient's ailments affecting the visual field. For example, patients suffering from macular degeneration experience a loss of vision because of impairments of the central retina and thus will have trouble seeing the visual field test pattern near the center fixation point. Since macular degeneration sufferers have peripheral vision, they would likely outline a central hole on the screen, and if they also had a relative visual field defect, they might trace an ever-smaller circle as the contrast of the visual field test pattern increased.

Referring again to FIG. 9, the visual field representation for a patient with "dry" macular degeneration is characterized by a peripheral area 910 of high contrast sensitivity. In the center of the visual field 912, the contrast sensitivity drops off significantly creating a hole in the visual field representation.

Figure 11:
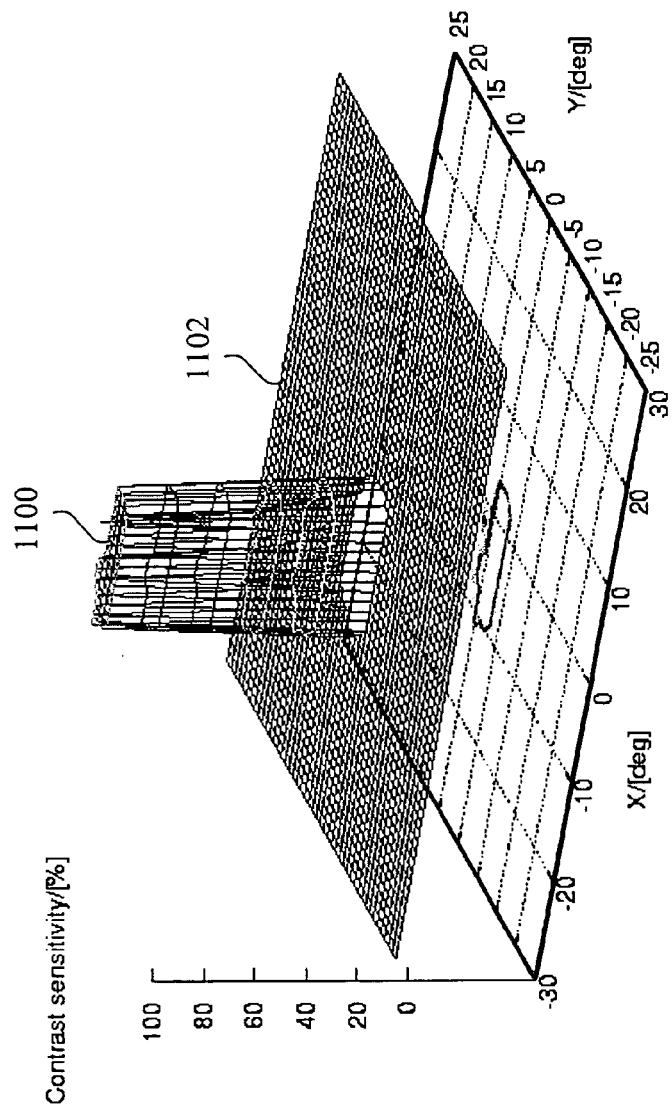
FIG. 11 is an exemplary visual field representation for a patient with glaucoma generated by an embodiment of a visual field measurement system according to the present invention.

FIG. 11 is an exemplary visual field representation for a patient with glaucoma generated by an embodiment of a visual field measurement system according to the present invention. A glaucoma patient is most likely to experience a loss of retinal contrast sensitivity at the periphery of the retina. Thus a glaucoma patient will outline a central area 1100 of high contrast sensitivity surrounded by an area 1102 of low contrast sensitivity.

The distinctive characteristics of visual field representations are used as the basis of a diagnostic tool employing pattern matching to determine a diagnosis from a visual field representation created from a patient's responses.

Figure 12:
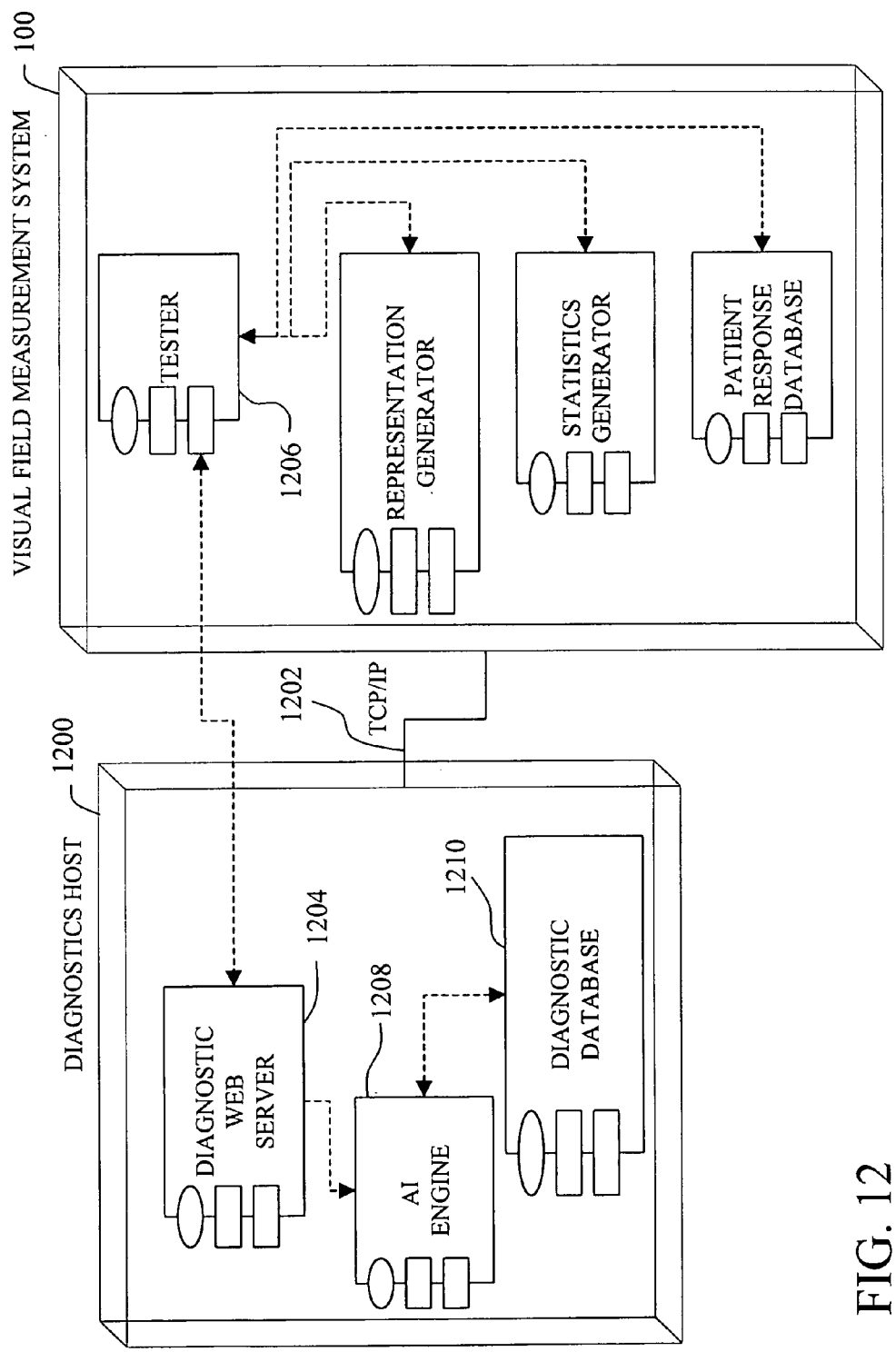
FIG. 12 is a deployment diagram of an embodiment of a distributed diagnostic system according to the present invention.

FIG. 12 is a deployment diagram of an embodiment of a distributed diagnostic system according to the present invention. A plurality of visual field measurement systems as exemplified by visual field measurement system 100 are operably coupled to a diagnostic host 1200 via a communications link 1202 adapted for communications using TCP/IP. The diagnostic host hosts a diagnostic Web server operably coupled to a previously described tester software module 1206 through the communications link. The diagnostic Web server is also operably coupled to a diagnostics generator such as an Artificial Intelligence (AI) engine 1208. The AI engine is also operably coupled to a diagnostic database. The diagnostic database includes a set of visual field representations mapped to a set of diagnoses.

Figure 13:
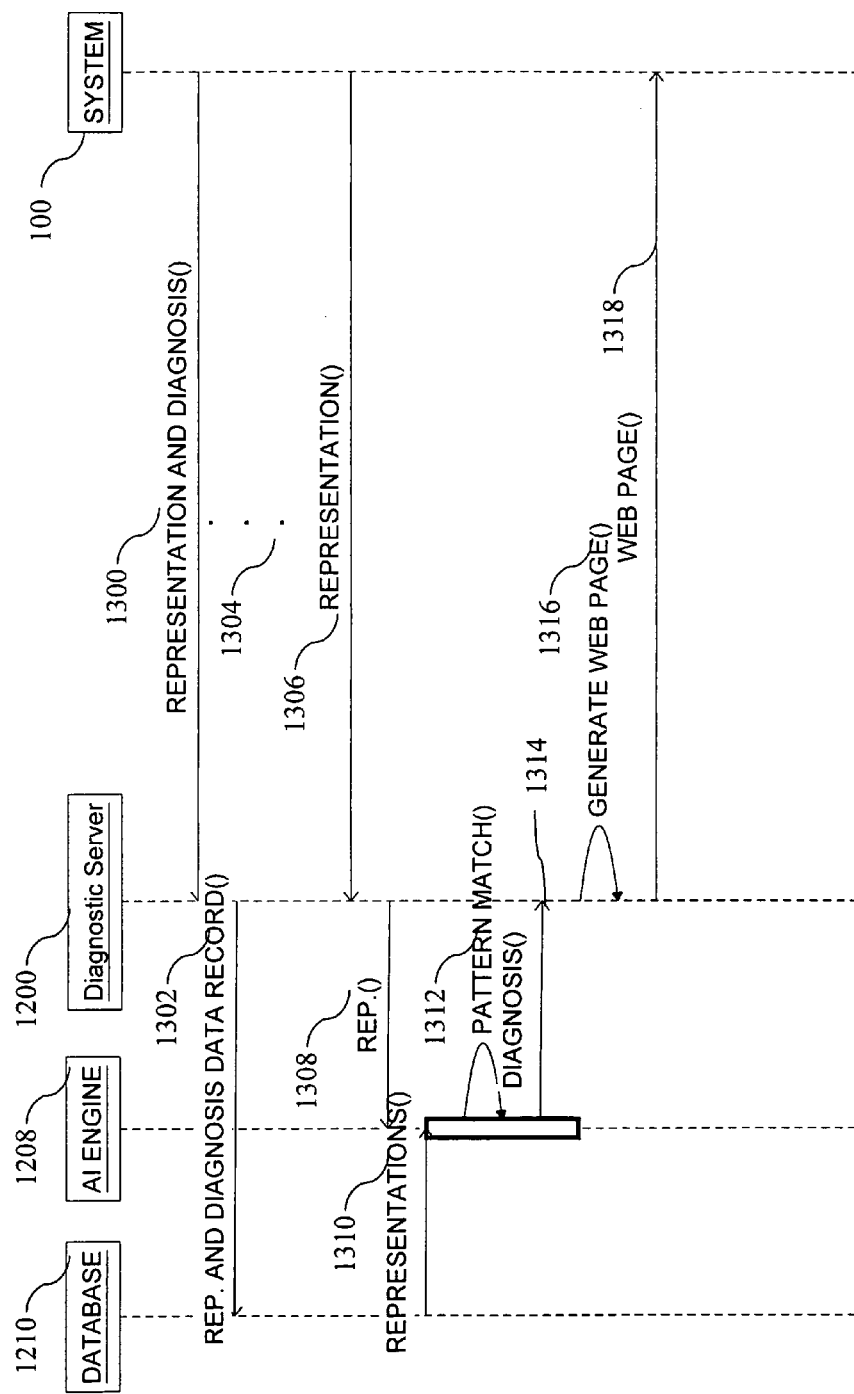
FIG. 13 is a sequence diagram of the operation of a distributed diagnostic system according to the present invention.

FIG. 13 is a sequence diagram of the operation of a distributed diagnostic system according to the present invention. In operation, a visual field measurement system 100 performs a visual field measurement acquiring a patient's responses and generates a visual field representation as previously described. A clinician performs an independent analysis of the patient and generates a diagnosis with a high confidence factor. The clinician transmits the visual field representation and diagnosis 1300 to a diagnostic server 1200. The diagnostic server generates a database record 1302 correlating the visual field representation and the diagnosis and puts the data record in the diagnostic database 1210.

This process is repeated 1304, building a set of a set of visual field representations mapped to a set of diagnoses in the diagnostic database.

To determine a diagnosis, a visual field measurement system 100 performs a visual field measurement acquiring a patient's responses and generates a visual field representation as previously described.

The visual field measurement system transmits the visual field representation 1306 to the diagnostic server and the diagnostic server transmits the visual field representation 1308 to the AI engine.

The AI engine receives the visual field representation and gets the set of visual field representations mapped to a set of diagnoses 1310 from the diagnostic database. The AI engine searches the set of visual field representations for visual field representations with a high correlation to the received visual field representation using pattern matching techniques 1312. If a matching database visual field representation is found, the AI engine transmits a diagnosis 1314 associated with the database visual field to the diagnostics Web server.

The diagnostic Web server generates 1316 a diagnostic Web page 1318 using the diagnosis and transmits the diagnostic Web page to the visual field measurement system.

Figure 20:
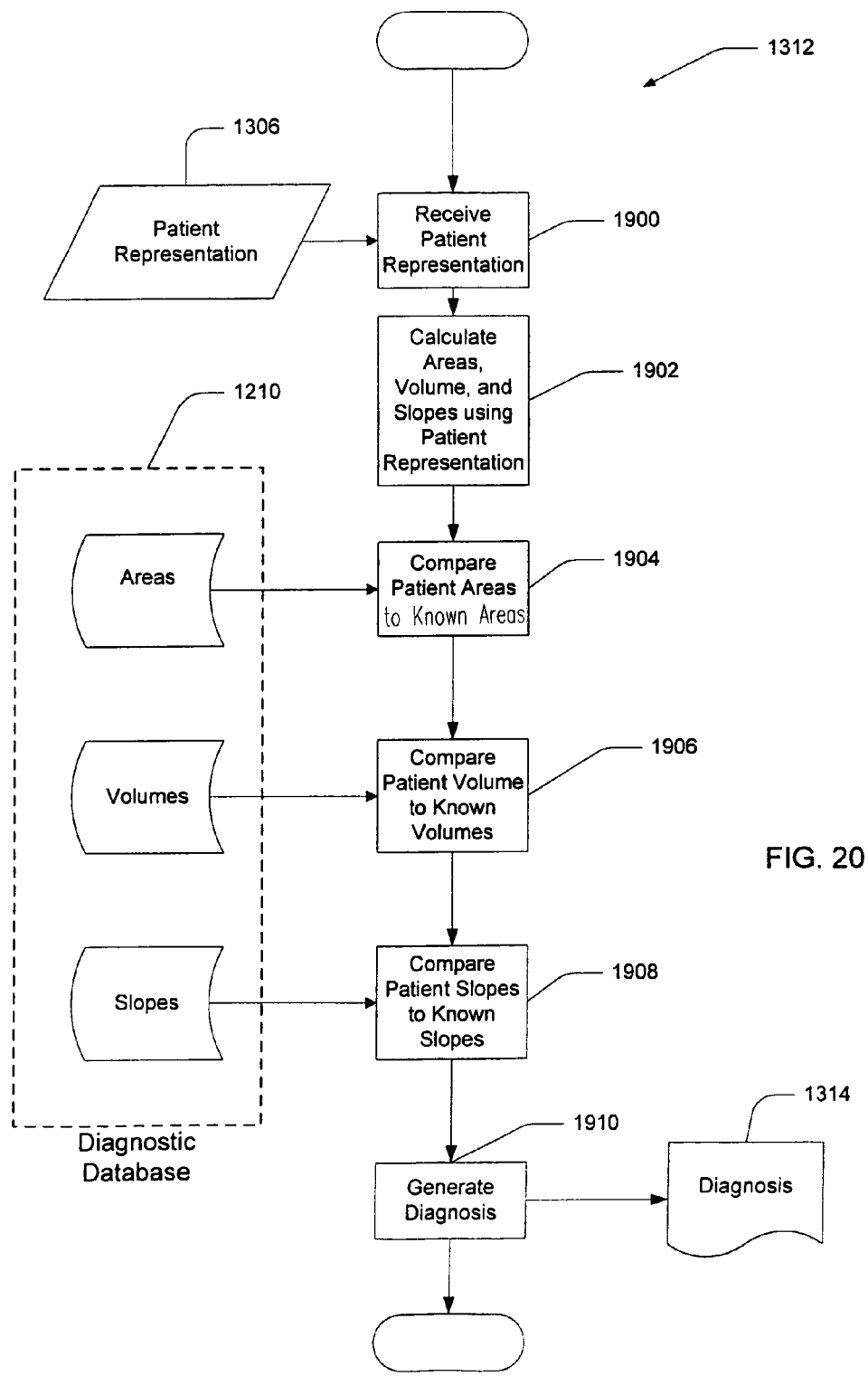
FIG. 20 is a process flow diagram of a diagnostic process in accordance with an exemplary embodiment of the present invention.

FIG. 20 is a process flow diagram of a diagnostic process in accordance with an exemplary embodiment of the present invention. A diagnostic process 1312 is one process used by an AI engine to detect and diagnose visual field defects. The diagnostic process receives (1900) a patient visual field representation 1306 from a visual field measurement system. The diagnostic process uses the patient visual field representation to calculate (1902) statistical values for the patient visual field representation as previously described. The statistical values may include the areas of visual field loss as a function of contrast sensitivity, overall volume of visual field loss as compared to a "normal" visual field representation, and slope distributions of scotoma boundaries.

The diagnostic process compares (1904) the areas of visual field loss as a function of contrast sensitivity calculated using the patient visual field representation to areas of visual field loss as a function of contrast sensitivity correlated to specific diseases 1905 stored in a diagnostic database 1210. The diagnostic process may also compare (1906)

overall volume of visual field loss calculated from the patient visual field representation to overall volumes of visual field loss correlated to specific diseases 1907 stored in the diagnostic database. The diagnostic process may also compare (1908) the slope distributions of scotoma boundaries calculated from the patient visual field representation to slope distributions of scotoma boundaries correlated to specific diseases 1909 stored in the diagnostic database.

The diagnostic process then uses the comparisons to generate (1910) a diagnosis 1314 of the cause of a patient's visual field defect. For example, if all the patient's statistical values match all of the statistical values correlated to a specific disease, the diagnostic process can determine with a high degree of certainty that the patient has that specific disease.

Figure 21:
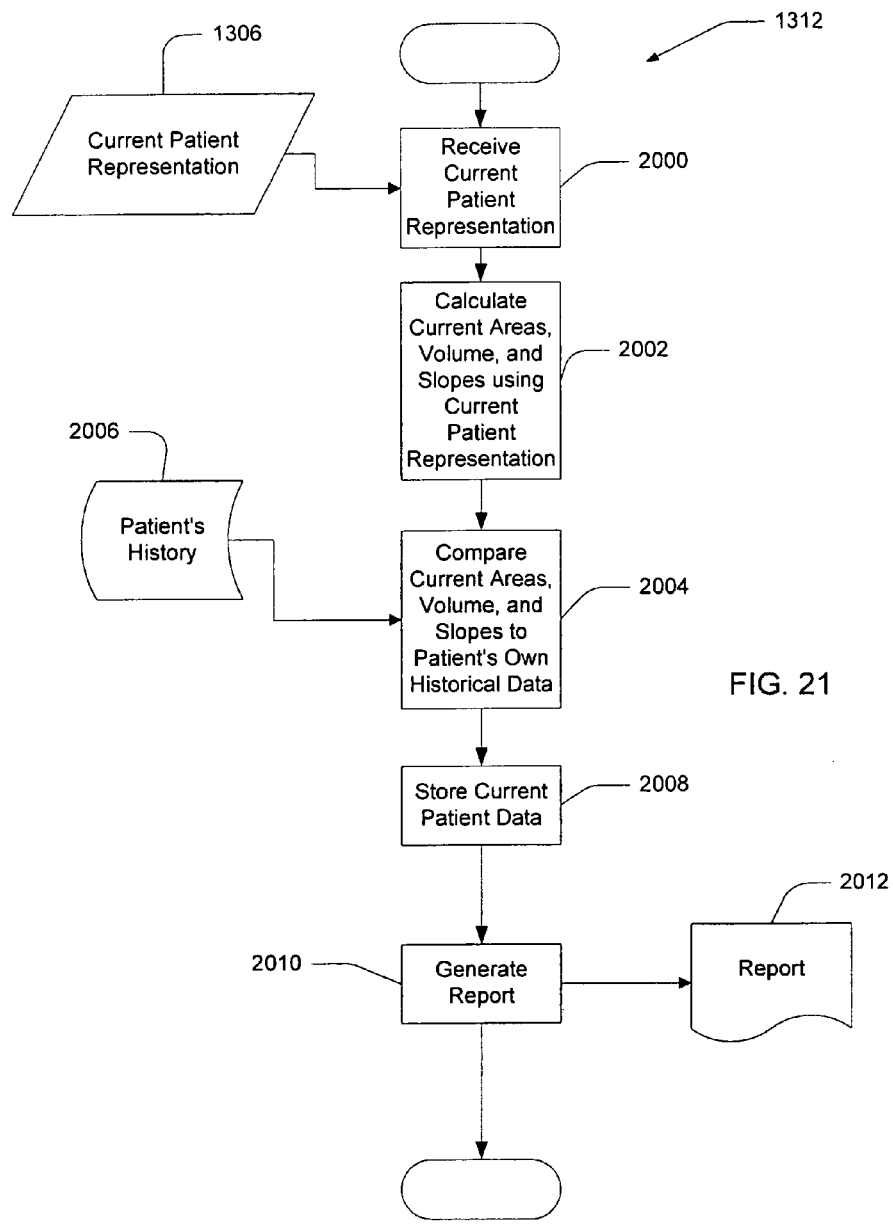
FIG. 21 is a process flow diagram of a patient monitoring process in accordance with an exemplary embodiment of the present invention.
Figure 14:
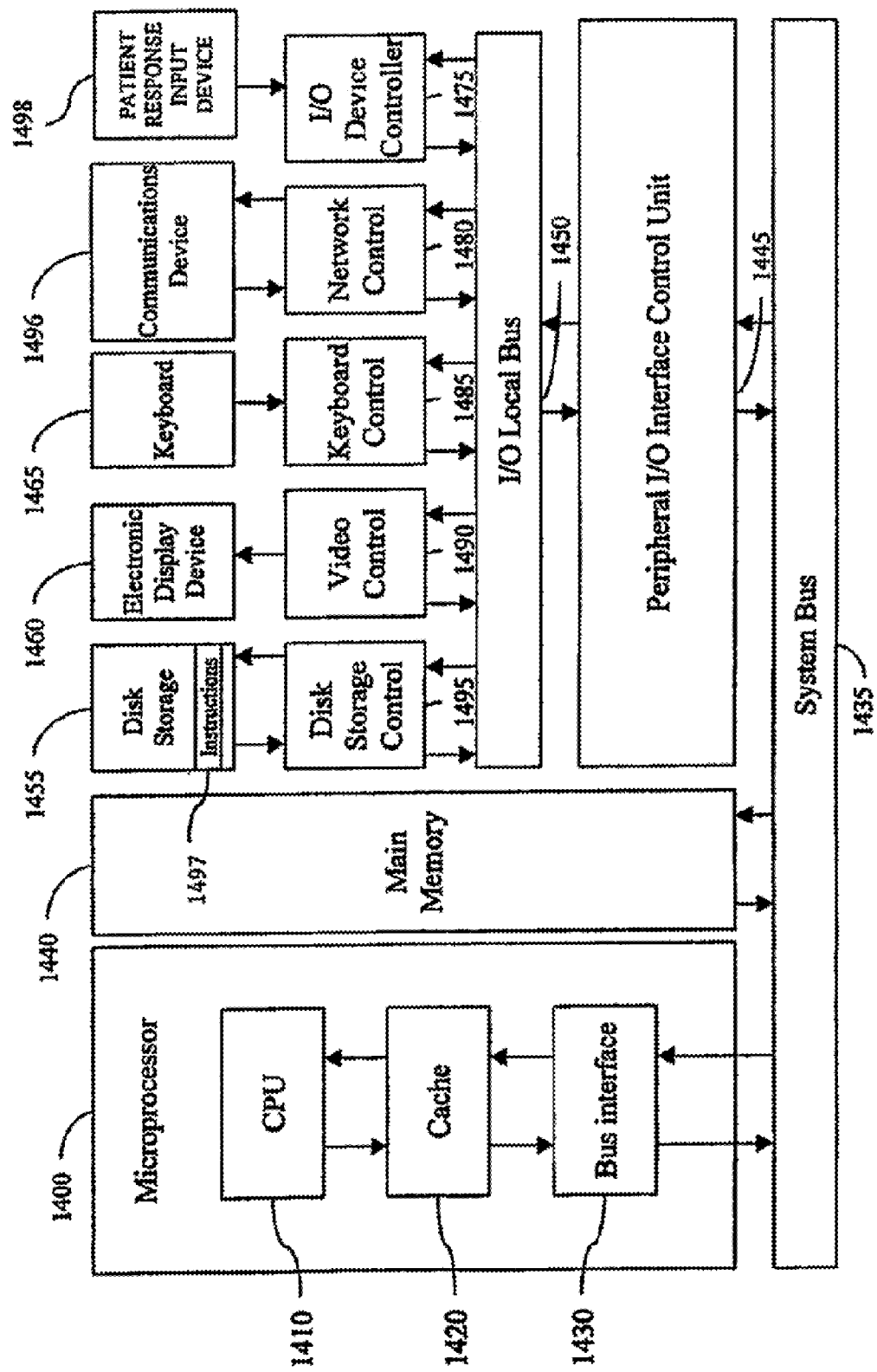

FIG. 21 is a process flow diagram of a patient monitoring process in accordance with an exemplary embodiment of the present invention. A patient monitoring process 2000 may be used by an AI engine to track the progression of an individual patient's visual field defect. The patient monitoring process receives (2001) a patient visual field representation 1306 from a visual field measurement system. The patient monitoring process uses the patient visual field representation to calculate (2002) statistical values for the patient visual field representation as previously described. The statistical values may include the areas of visual field loss as a function of contrast sensitivity, overall volume of visual field loss as compared to a "normal" visual field representation, and slope distributions of scotoma boundaries.

The patient monitoring process compares (2004) the patient's areas of visual field loss as a function of contrast sensitivity calculated using the patient visual field representation to areas of visual field loss as a function of contrast sensitivity, overall volume of visual field loss, and slope distributions of scotoma boundaries calculated from the patient visual field representation to the patient's own history 2006. The current patient values are then stored (2008) as part of the patient's history for further use. The diagnostic process then uses the comparisons to generate (2010) a report 2012 of the progression of the patient's visual field defect.

Figure 14:
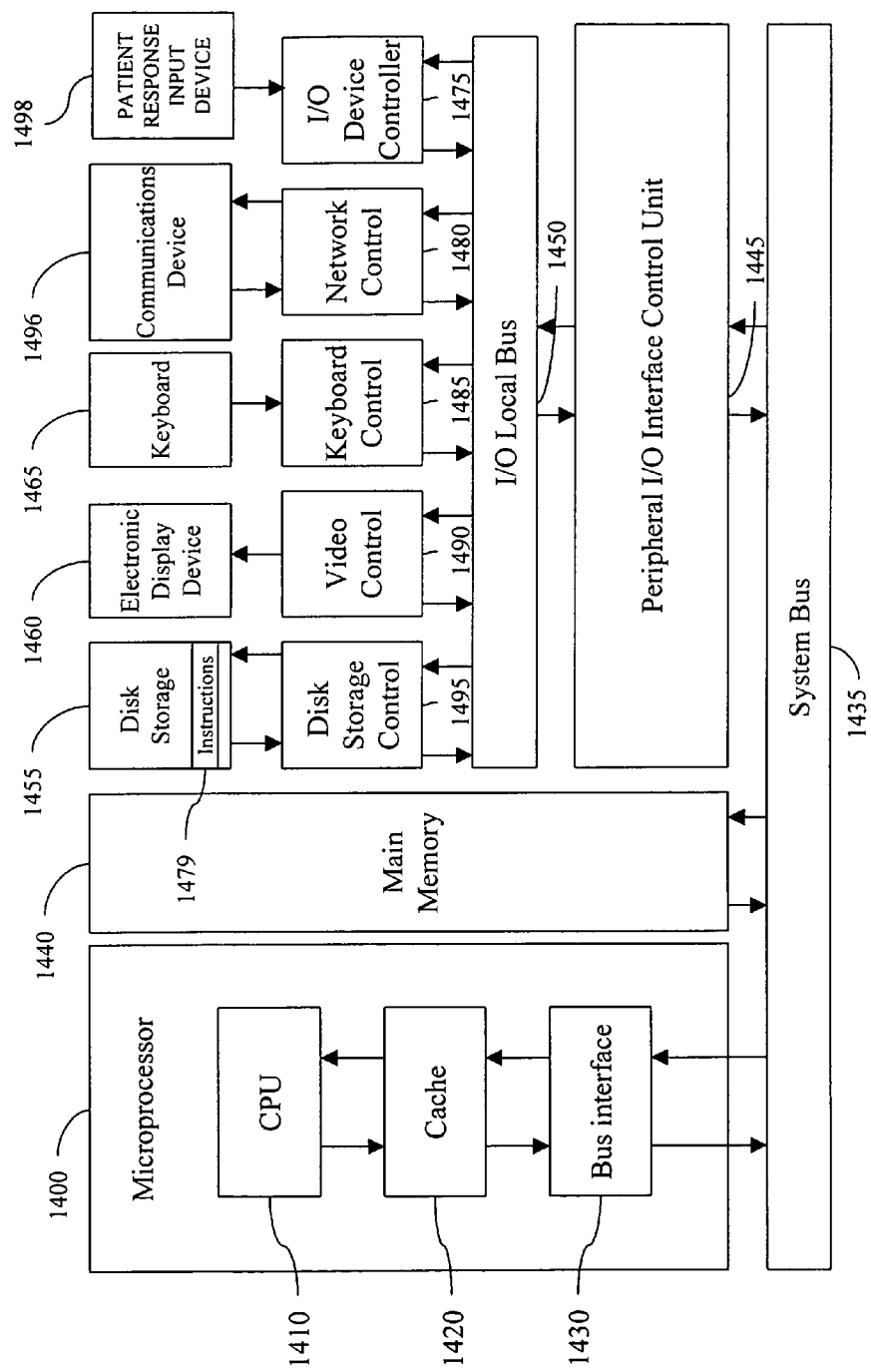
FIG. 14 is an architecture diagram for a general purpose computer suitable for use as a visual field measurement system according to the present invention.

FIG. 14 is an architecture diagram for a general purpose computer suitable for use as a visual field measurement system according to the present invention. A microprocessor 1400, including a Central Processing Unit (CPU) 1410, a memory cache 1420, and a bus interface 1430, is operably coupled via system bus 1435 to a main memory 1440 and an I/O control unit 1445. The I/O interface control unit is operably coupled via an I/O local bus 1450 to a disk storage controller 1495, a video controller 1490, a keyboard controller 1485, a network controller 1480, and an I/O device controller 1475. The disk storage controller is operably coupled to a disk storage device 1455 for storage and retrieval of computer instructions 1497 and data. The video controller is operably coupled to an electronic display device 1460 for display of visual field test patterns to a patient. The keyboard controller is operably coupled to a keyboard 1465 for input of commands to the visual field measurement system. The network controller is operably coupled to a communications device 1496. The communications device is adapted to allow software objects hosted by the general purpose computer to communicate via a network with other software objects. The I/O device controller is operably coupled to a patient response input device 1498 for input of patient responses to the visual field test pattern.

Computer program instructions 1497 implementing software objects comprising a visual field measurement system are stored on the disk storage device until the microprocessor retrieves the computer program instructions and stores them in the main memory. The microprocessor then executes the computer program instructions stored in the main memory to instantiate a visual field measurement system.

Although this invention has been described in certain specific embodiments, many additional modifications and variations would be apparent to those skilled in the art. It is therefore to be understood that this invention may be practiced otherwise than as specifically described. Thus, the present embodiments of the invention should be considered in all respects as illustrative and not restrictive, the scope of the invention to be determined by claims supported by this application and the claim's equivalents rather than the foregoing description.

What is claimed is:

1. A method of objectively characterizing a patient's visual field, comprising:
   repeating steps a and b for a plurality of varying contrast levels and a plurality of corresponding patient response signals:
      a) presenting a visual field test pattern to the patient using an electronic display device, the visual field test pattern presented at a contrast level selected from the plurality of varying contrast levels;
      b) receiving a corresponding patient response signal; and
   generating a characterization of the patient's visual field using the plurality of contrast levels and the plurality of corresponding patient response signals.

2. The method of claim 1, wherein the characterization includes a statistical description of a boundary of a visual field defect.

3. The method of claim 2, wherein the statistical description includes a percentage of retinal contrast sensitivity loss over degrees of visual field expressed as a slope of a line.

4. The method of claim 3, wherein the statistical description further includes a mean of a plurality of slopes.

5. The method of claim 3, wherein the statistical description further includes a distribution of a plurality of slopes.

6. The method of claim 1, wherein the characterization includes an area of a visual field defect at a specified contrast sensitivity.

7. The method of claim 1, wherein the characterization includes a volume of a visual field defect.

8. The method of claim 1, the method further comprising generating a diagnosis by comparing the statistical characterization to a set of statistical characterizations associated with known causes of visual field defects.

9. The method of claim 1, the method further comprising monitoring the progression of a visual field defect in the patient's visual field by comparing the statistical characterization to a set of statistical characterizations associated with the patient.

10. A data processing apparatus for objectively characterizing a patient's visual field, comprising:
   a processor; and
   a memory coupled to the processor, the memory having program instructions executable by the processor stored therein, the program instructions including:
      repeating steps a and b for a plurality of varying contrast levels and a plurality of corresponding patient response signals:
         a) presenting a visual field test pattern to the patient using an electronic display device, the visual field test pattern presented at a contrast level selected from the plurality of varying contrast levels;

b) receiving a corresponding patient response signal; and generating a characterization of the patient's visual field using the plurality of contrast levels and the plurality of corresponding patient response signals.

11. The data processing apparatus of claim 10, wherein the characterization includes a statistical description of a boundary of a visual field defect.

12. The data processing apparatus of claim 11, wherein the statistical description includes a percentage of retinal contrast sensitivity loss over degrees of visual field expressed as a slope of a line.

13. The data processing apparatus of claim 12, wherein the statistical description further includes a mean of a plurality of slopes.

14. The data processing apparatus of claim 11, wherein the statistical description further includes a distribution of a plurality of slopes.

15. The data processing apparatus of claim 10, wherein the characterization includes an area of a visual field defect at a specified contrast sensitivity.

16. The data processing apparatus of claim 10, wherein the characterization includes a volume of a visual field defect.

17. The data processing apparatus of claim 10, the program instructions further including generating a diagnosis by comparing the statistical characterization to a set of statistical characterizations associated with known causes of visual field defects.

18. The data processing apparatus of claim 10, the program instructions further including monitoring the progression of a visual field defect in the patient's visual field by comparing the statistical characterization to a set of statistical characterizations associated with the patient.

* * * * *

UNITED STATES PATENT AND TRADEMARK OFFICE
CERTIFICATE OF CORRECTION

| | | |
|---|---|---|
| PATENT NO. | : 7,101,044 B2 | |
| APPLICATION NO. | : 10/430367 | |
| DATED | : September 5, 2006 | |
| INVENTOR(S) | : Fink | |

It is certified that error appears in the above-identified patent and that said Letters Patent is hereby corrected as shown below:

On the Title Page (*) Notice — After "by 367 days.", Insert --This patent is subject to a Terminal Disclaimer.--

(60) Related U.S. Application Data — Delete "60/251,957, filed on December 7, 2000", Insert --60/251,957, filed on December 6, 2000--

(56) References Cited
U.S. Patent Documents
6,572,229... — Delete "B1", Insert --B2--

In the Drawings

FIG. 14, Sheet 14 of 21 — Delete Drawing Sheet 14 and substitute therefore the Drawing Sheet, consisting of Fig. 14, as shown on the attached page Signed and Sealed this Twenty-fourth Day of April, 2007

JON W. DUDAS
*Director of the United States Patent and Trademark Office*